United States Patent
Rose

(10) Patent No.: US 11,498,941 B2
(45) Date of Patent: Nov. 15, 2022

(54) CHROMATOGRAPHY

(71) Applicant: UCB BIOPHARMA SRL, Brussels (BE)

(72) Inventor: Michael Harry Rose, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 395 days.

(21) Appl. No.: 16/629,609

(22) PCT Filed: Jul. 16, 2018

(86) PCT No.: PCT/EP2018/069298
§ 371 (c)(1),
(2) Date: Jan. 9, 2020

(87) PCT Pub. No.: WO2019/016154
PCT Pub. Date: Jan. 24, 2019

(65) Prior Publication Data
US 2020/0331960 A1    Oct. 22, 2020

(30) Foreign Application Priority Data

Jul. 17, 2017    (GB) ..................... 1711481

(51) Int. Cl.
*C07K 1/22* (2006.01)
*B01D 15/18* (2006.01)
(Continued)

(52) U.S. Cl.
CPC ............ *C07K 1/22* (2013.01); *B01D 15/1814* (2013.01); *B01D 15/245* (2013.01);
(Continued)

(58) Field of Classification Search
CPC ... C07K 1/22; C07K 1/34; C07K 1/18; C07K 1/16; B01D 15/1814; B01D 15/245; B01D 15/247; B01D 15/3809
See application file for complete search history.

(56) References Cited

U.S. PATENT DOCUMENTS 8,569,464 B2 * 10/2013 Moya ...................... C07K 1/32
530/421
9,803,004 B2    10/2017 Adams et al.
(Continued)

FOREIGN PATENT DOCUMENTS

JP    S5940161        3/1984
JP    61270658 A * 11/1986 ............. G01N 30/44
(Continued)

OTHER PUBLICATIONS

Albanese et al., Industrial-Scale Biochromatography cols. Address Challenging Purification Needs, Feb. 2011, (Year: 2011).*
(Continued)

*Primary Examiner* — Emmanuel E Duke
(74) *Attorney, Agent, or Firm* — Saliwanchik, Lloyd & Eisenschenk

(57) ABSTRACT

The present invention is in the field of purification and protein purification in particular. The invention provides improved techniques for the industrial-scale purification of proteins and other biomolecules. More specifically, it relates to a process for the purification of a compound of interest, such as a protein, preferably an antibody or an antibody fragment using a chromatography step, preferably a semi-continuous chromatography step.

29 Claims, 19 Drawing Sheets

(51) Int. Cl.
    *B01D 15/24*    (2006.01)
    *B01D 15/38*    (2006.01)
    *C07K 1/34*    (2006.01)

(52) U.S. Cl.
    CPC ....... *B01D 15/247* (2013.01); *B01D 15/3809* (2013.01); *C07K 1/34* (2013.01)

(56) References Cited

U.S. PATENT DOCUMENTS

| | | |
|---|---|---|
| 10,023,631 B2 | 7/2018 | Adams et al. |
| 2014/0348845 A1 | 11/2014 | Bill, Jr. et al. |

FOREIGN PATENT DOCUMENTS

| | | |
|---|---|---|
| JP | S61270658 | 11/1986 |
| WO | WO 2013/068571 | 5/2013 |
| WO | WO 2014/158231 | 10/2014 |
| WO | WO 2016/009221 | 1/2016 |
| WO | WO 2017/140881 | 8/2017 |

OTHER PUBLICATIONS

Kontermann, R. E. "Dual targeting strategies with bispecific antibodies" *mAbs*, Mar./Apr. 2012, pp. 182-197, vol. 4, Issue 2.

Kuo, W.-H. K. et al. "A new strategy for the on-column exopeptidase cleavage of poly-histidine tagged proteins" *Journal of Chromatography B*, 2011, pp. 3028-3033, vol. 879, No. 28.

Mahajan, E et al. "Improving affinity chromatography resin efficiency using semi-continuous chromatography" *Journal of Chromatography A*, 2012, pp. 154-162, vol. 1227.

Persson, O. et al. "Design of two-column batch-to-batch recirculation to enhance performance in ion-exchange chromatography" *Journal of Chromatography A*, 2018, pp. 112-121, vol. 1531.

Written Opinion in International Application No. PCT/EP2018/069298, dated Dec. 13, 2018, pp. 1-6.

Charton, F. et al. "Recycling in preparative liquid chromatography" *Journal of Chromatography A*, 1994, pp. 13-31, vol. 687, No. 1.

* cited by examiner

FIGURE 17

|  | Retained pool (Early Cation exchange peak) | | Retained pool (Late Cation Exchange Peak of interest) | |
|---|---|---|---|---|
| Cycle | Non-Fab (arbitrary units) | Fab (mg) | Non-Fab (arbitrary units) | Fab (mg) |
| 1 | 6083.10 | 2.26 | 2404.45 | 29.63 |
| 2 | 8023.39 | 7.78 | 3067.92 | 36.24 |
| 3 | 8380.01 | 10.50 | 3091.54 | 36.39 |
| 4 | 8476.27 | 11.73 | 2993.96 | 37.17 |
| 5 | 2525.75 | 10.53 | 2899.82 | 33.48 |
| 6 | 2800.57 | 9.97 | 2813.99 | 36.39 |
| 7* | 8202.97 | 11.89 | 2871.66 | 39.72 |

FIGURE 18

|  | Retained pool (Fab peak of interest) | |
|---|---|---|
| Cycle | Non-Fab | Fab (mg) |
| 1 | 100% | 100% |
| 2 | 128% | 122% |
| 3 | 129% | 123% |
| 4 | 125% | 125% |
| 5 | 121% | 113% |
| 6 | 117% | 123% |
| 7* | 119% | 134% |

FIGURE 19

|  | Retained pool (Fab peak of interest) | |
|---|---|---|
| Cycles | Non-Fab | Fab (mg) |
| 1 | 100% | 100% |
| 2 | 104% | 96% |
| 3 | 105% | 96% |
| 4 | 99% | 101% |
| 5 | 107% | 94% |
| 6 | 95% | 105% |
| 7* | 89% | 112% |

CHROMATOGRAPHY

CROSS-REFERENCE TO RELATED APPLICATION

This application is the U.S. national stage application of International Patent Application No. PCT/EP2018/069298, filed Jul. 16, 2018.

FIELD OF THE INVENTION

The present invention is in the field of purification and protein purification in particular. The invention provides improved techniques for the industrial-scale purification of proteins and other biomolecules. More specifically, it relates to a process for the purification of a compound of interest, such as a protein, preferably an antibody or an antibody fragment using a chromatography step, preferably a semi-continuous chromatography step.

BACKGROUND OF THE INVENTION

The large-scale, economic purification of proteins and nucleic acid molecules is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors. The protein of interest must be isolated from the mixture of compounds fed to the cells and from the by-products of the cells themselves (feed stream) to purity sufficient for use as a human therapeutic. The standards set by health authorities for proteins intended for human administration regarding impurities from the feed stream are very high.

Industrial protein purification is typically carried out on a very large scale. Commercial bioreactors for producing therapeutic proteins such as antibodies typically contain hundreds, thousands or even tens of thousands of litres of culture medium. Cells are typically grown to a desired level which may be determined by for example measuring the optical density of the growth medium at an appropriate wavelength such as around 600 nm, with increasing optical density corresponding to increased cellular concentration in the growth medium.

Once the desired level has been reached, a crude protein extract is typically prepared. The crude extract may be prepared by conventional techniques such as lysis, filtration and/or initial concentration, etc to produce the crude extract. The high volumes of culture medium to be treated from commercial bioreactors generate correspondingly large volumes of crude extract. For example a 2000 litre cell culture may typically yield crude protein extract volumes of hundreds of litres, often containing kilograms of the desired protein. The large volumes of crude protein extract generated in industrial protein synthesis techniques require dedicated purification techniques. Laboratory scale techniques intended for the purification of very small volumes (typically tens to hundreds of milliliters) of crude protein extract (feedstock) are typically poorly scalable to industrial levels, due to difficulties in preventing contamination, the need for efficient processing, requirements for automation, etc. Accordingly, industrial scale purification techniques have been developed for the large scale purification of biomolecules such as proteins.

Protein purification is often achieved used chromatographic techniques, such as affinity chromatography (which separates proteins on the basis of a reversible interaction between the protein of interest and a specific ligand coupled to a chromatography matrix); ion exchange chromatography (which separates proteins on the basis of the non-specific electrostatic interaction of their charged groups with oppositely charged molecules attached to a chromatography matrix); displacement chromatography (which separates proteins based on their dynamic affinity for the chromatography matrix); and size exclusion chromatography (which separates proteins based on their size). One common feature of these and other chromatographic techniques used to separate biomolecules is the presence of a suitable separation matrix, often referred to as a resin. Chromatography matrices are typically expensive and have a limited life in use, due to irreversible contamination, degradation of the matrix material, undesired reactions at functional groups on the matrix, etc. The large volumes of crude protein extract that need to be processed in industrial protein purification require correspondingly large amounts of chromatography matrix. The high cost of such matrices is a driver to maximize the efficiency of the purification technique as far as possible.

A further aspect that has to be considered in designing protein purification techniques is the properties of the impurities which need to be removed from the protein of interest. Typically, crude protein extracts contain impurities having significantly different characteristics of binding to the chromatography matrix compared to the protein of interest. Such impurities are typically easily removed. Other impurities typically have similar binding characteristics to the protein of interest. Typically, these impurities may co-elute from the matrix at least in part with the desired protein, such that a degree of overlap is observed. Accordingly, feedstock comprising the protein of interest and impurities can typically be considered as comprising three components: the product of interest (i.e. the product biomolecule); impurities which bind to the chromatography matrix more weakly than the product of interest; and impurities which bind to the chromatography matrix more strongly than the product of interest.

Traditional techniques to separate such components rely on batch column chromatography. The feedstock is loaded onto a column and the column effluent collected in small fractions. Components of the feedstock which bind most weakly to the column elute first. Accordingly, in addition to fractions containing only the product of interest, leading fractions comprise both the product of interest and impurities which bind to the chromatography matrix less strongly than the product of interest; and trailing fractions comprise both the product of interest and impurities which bind to the chromatography matrix more strongly than the product of interest. Due to the strict purity requirements for proteins to be used in therapeutic applications, these "overlap fractions" (i.e. the leading and trailing fractions) are traditionally discarded, decreasing the efficiency of the overall purification process.

A further aspect of traditional chromatography techniques is the concept of overload. Chromatography matrices have a limited binding capacity. Once this capacity is reached, excess product of interest cannot bind to the matrix and is typically lost as "overload". In addition, the selectivity of the matrix typically decreases as the binding capacity is approached. In traditional techniques, overload protein samples can be lost or have to be further processed, increasing the risk of contamination.

One standard industrial technique used is multicolumn countercurrent solvent gradient purification (MCSGP). MCGSP is a chromatography technique which relies on multiple chromatography columns to purify crude protein extracts to a desired level. In MCGSP, multiple chromatography columns are switched in position opposite to the flow direction of the crude protein extract. In summary, a crude protein extract is loaded onto a first column such that the protein of interest binds to the chromatography matrix (the resin). Once weakly absorbing impurities have been washed from the matrix, elution of the protein of interest is begun. Pure fractions of the desired protein are retained, whilst both leading and trailing overlap fractions are directed to a second column, and combined with further feed (crude protein solution). The process is then repeated on the second column, with the overlap fractions directed to a further column. In theory, the overlap fractions can be redirected back to the first column, although in practice a series of columns is typically used to allow time for cleaning, re-equilibration, etc of each column prior to re-use. In this manner, the desired protein may be obtained in high purity, as the impure overlap fractions are subjected to repeated purification cycles.

Whilst MCSGP is intended for large scale use in industry, it is associated with significant disadvantages. As will be apparent from the above summary, MSCGP requires a minimum of two matched chromatography columns, and in practice more than two columns are often used in order to maximize the efficiency of the process as far as possible. The high cost of the matrix (resins) used in chromatography means that the requirement for multiple columns adds significantly to the cost of protein production. Another issue with the MSCGP technique is the highly complex nature of the equipment required, as in addition to the multiple matched columns, sophisticated flow control apparatus and control software, as well as additional chromatography hardware including in-line mixers, pumps, valves, detectors and housing for each additional column are required, all of which add cost, increase the probability of part failure, increase the complexity of validation processes and complicate diagnosis of errors. A further issue with the MSCGP technique is the requirement for the process to be operated continuously. This can be problematic when the time required for purification to take place (e.g. of crude protein extracts from large culture volumes) cannot be concluded in accordance with standard working practice; e.g. requiring operators to work around the clock for extended periods of time. Still a further issue is that in order to achieve adequate separation, slow flow rates and/or large matrix volumes are required.

In view of such considerations, the inventors have recognized the need for improved techniques for large scale protein purification. The invention therefore provides an improved method for purifying proteins and other biomolecules on an industrial scale, and is intended to solve some or all of the above problems.

BRIEF DESCRIPTION OF THE INVENTION

Whilst MCSGP has been applied in large scale industrial protein purification, the inventors have recognized that significant benefits arise from the separation of the product of interest (i.e. the product biomolecule) and the recycling of overlap and optionally overload fractions on a single chromatography matrix, e.g. on a single column. The use of a single matrix is associated with significant advantages over prior art techniques using multiple columns. The cost of the matrix (resin) required can be significantly reduced as only one column rather than multiple columns is required. The complexity of the equipment (e.g.) flow control apparatus and control software required to operate the columns is also significantly decreased, and the need for chromatography hardware such as in-line mixers, pumps, valves, detectors etc reduced. Importantly, the process can be operated discontinuously (asynchronously), which allows purifications to be operated around working days, and even to be interrupted for extended periods of time. Adequate separation can also be achieved using relatively high flow rates and/or low matrix volumes as compared with previously known techniques.

Previously, the inventor reported in WO 2017/140881 a chromatographic process for purifying proteins from mixtures. The process reported in WO 2017/140881 involves loading a chromatography matrix such that the binding capacity of the matrix is exceeded, causing flow-through containing unbound protein to pass through the matrix, and subsequently reloading the flow-through to the matrix in a further operational chromatography cycle. The inventor has now developed a new chromatographic technique which involves loading feed from a feedstock onto a chromatography matrix, eluting the product, and reloading fractions of the eluate comprising both the product biomolecule and at least one impurity to the matrix. Such methods are distinct from the methods reported in WO 2017/140881 and are associated with significant beneficial effects including improved purification yields. The methods of the present invention are particularly suited to "polishing" steps following initial partial purification of feedstock from a crude extract.

The present invention thus provides a process for the purification of a product biomolecule (a compound of interest and a protein of interest in particular) which involves more efficient and cost effective use of chromatography matrices while maintaining or improving yield and purity of the purified compound.

Accordingly, the invention provides an industrial-scale process for the purification of a product biomolecule from a feedstock comprising the product biomolecule and at least one impurity, the process comprising the steps of:
  a) loading feed from the feedstock to a chromatography matrix such that the product biomolecule binds to the chromatography matrix;
  b) eluting the product biomolecule from the chromatography matrix in an eluate by applying an elution solution to the chromatography matrix;
    wherein the eluate comprises:
      a first fraction comprising purified product biomolecule; and
      a second fraction comprising both the product biomolecule and at least one impurity, the second fraction comprising one or more leading and/or trailing fraction(s);
    and wherein the first fraction is collected separately from the second fraction;
  c) holding the second fraction in one or more container;
  d) loading the second fraction from the container(s) and additional feed from the feedstock to the chromatography matrix such that the product biomolecule in the second fraction binds to the chromatography matrix; wherein the additional feed is loaded simultaneously with or sequentially to the second fraction; and
  e) eluting the product biomolecule from the chromatography matrix in an eluate by applying an elution solution to the chromatography matrix, wherein the eluate comprises purified product biomolecule;

wherein the chromatography matrix in step (a), step (b), step (d) and step (e) is the same chromatography matrix.

Preferably, in the invention, the product biomolecule is a protein, an antibody, an antibody fragment, a polynucleotide or a polypeptide.

Also provided is a process according to the invention further comprising formulating the purified product biomolecule with a pharmaceutically acceptable excipient, diluent or adjuvant. The invention also provides a purified product biomolecule obtainable by the process of the invention.

DESCRIPTION OF THE FIGURES

FIG. 2 depicts an example of the process of the invention. After load of the feedstock to the chromatography matrix, the first fraction containing purified product biomolecule is eluted. The second fraction comprises the leading and/or trailing fractions (defined herein) which are optionally processed (e.g. by dilution) prior to reloading onto the chromatography matrix. The cycle is repeated multiple times. Although FIG. 2 depicts both trailing and leading fractions being reloaded those skilled in the art will appreciate that the method of the invention does not require both fractions to be so reloaded—e.g. only one of the trailing (following) and/or leading (preceding) fractions may be re-loaded onto the matrix.

FIG. 3 shows another example of the process of the invention. In the process shown in FIG. 3 the at least one preceding (leading) fraction and/or the at least one following (trailing) fraction are processed prior to re-loading them separately to the same chromatography matrix in the following operational chromatography cycle.

In the process shown in FIG. 4 the at least one preceding (leading) fraction and the at least one following (trailing) fraction are combined and processed as a combined fraction prior to re-loading to the same chromatography matrix in the following operational chromatography cycle.

Figure 1:
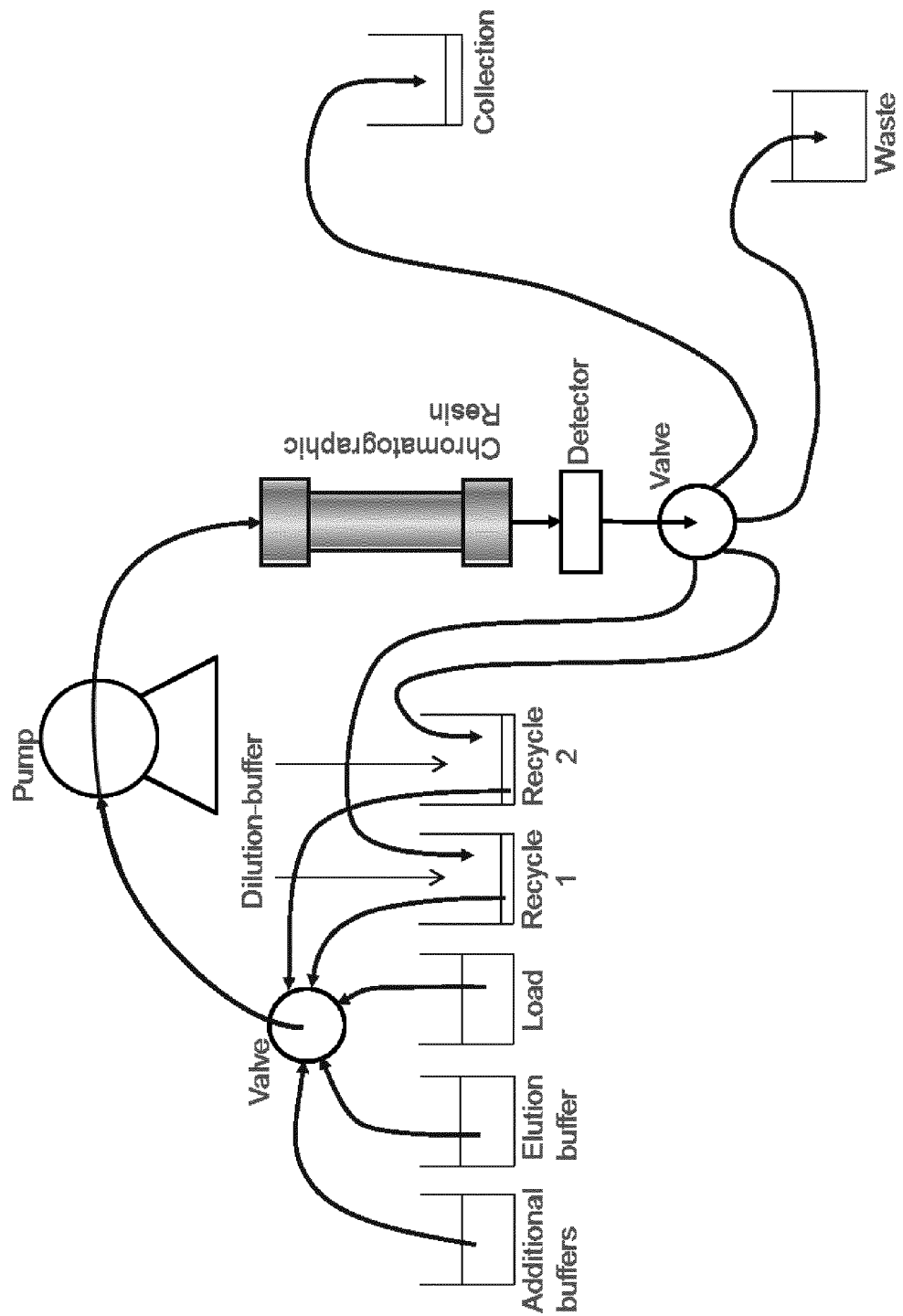
FIG. 1 shows a schematic diagram of a setup for use in the process of the present invention. Various liquid buffer components are held in tanks and are sequentially pumped via a valve through a porous chromatographic matrix. After emerging from the chromatography matrix, fractions of the eluate pass through a detector which analyses discrete volumes of the eluate which are also referred to herein as fractions of the eluate. The "first fractions" comprising purified product biomolecule (i.e. those one or more fractions of the eluate showing the desired characteristics for the compound of interest such as concentration of said compound or purity of said compound), are collected. From the remaining fractions, "second fractions" comprising both the product biomolecule and at least one impurity (i.e. those fractions not showing the desired characteristics but still containing the compound of interest and being in principle suitable for further processing) are collected for re-loading to the same chromatography matrix. In the set-up of FIG. 1, there are two fractions which are separately collected in containers "Recycle 1" and "Recycle 2".
Figure 2:
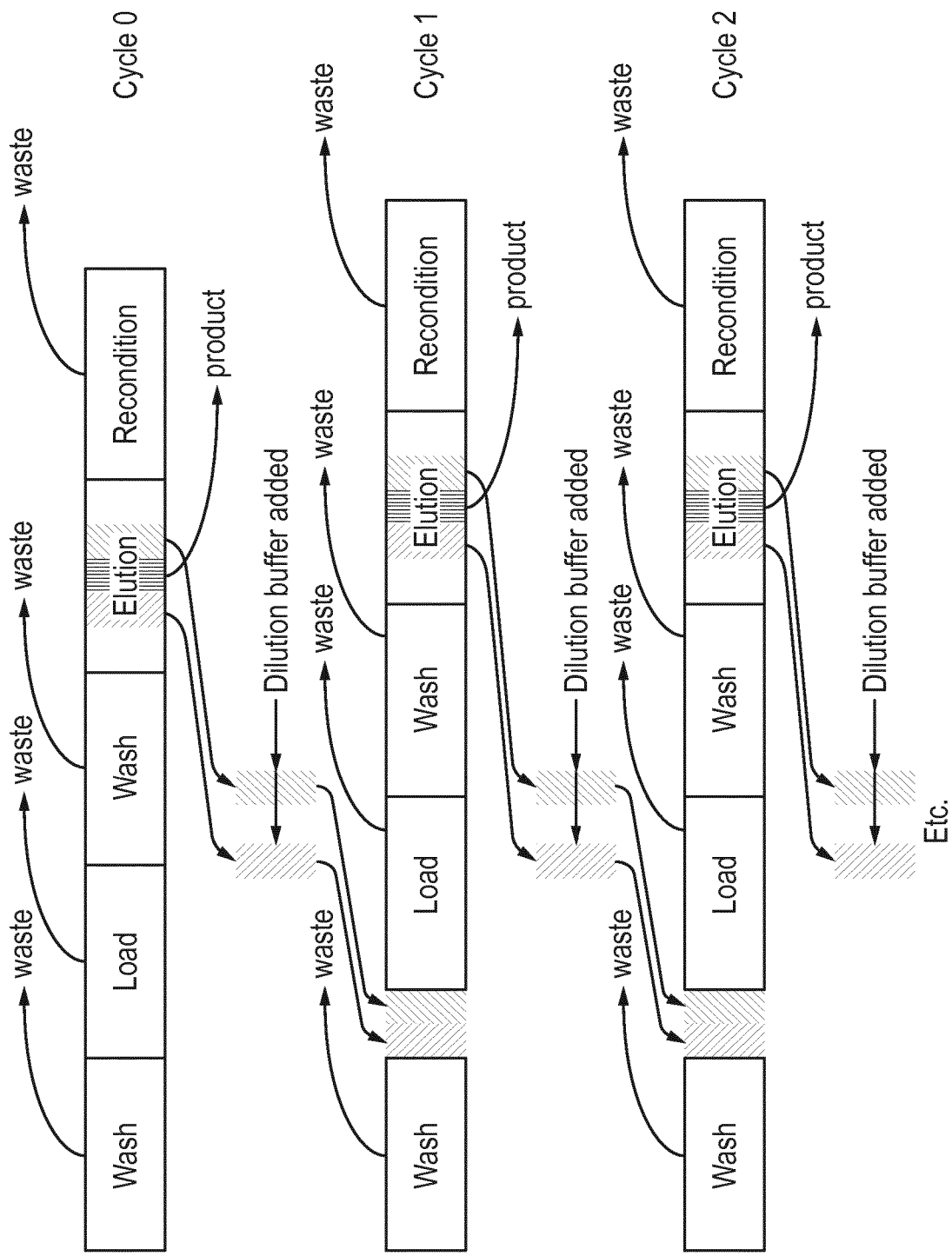
FIGS. 2 to 7 show diagrams of processes according to the invention. A typical chromatographic separation may involve a binding stage where the product biomolecule (protein of interest/target compound) binds to an immobilised matrix, and an elution stage where the product biomolecule (target compound) is chemically removed from the matrix. In between there are typically wash and conditioning steps to remove further impurities and maintain the quality of the matrix, during which these materials are typically directed to waste. In the processes shown in FIGS. 2 to 7, according to the instant invention a mixture comprising the product biomolecule (compound of interest) and at least one impurity is loaded to a chromatography matrix, said loaded chromatography matrix is washed and the product biomolecule (compound of interest) is eluted from the chromatography matrix. The one or more of the "first fraction(s)" of the eluate comprising purified product biomolecule (i.e. those fractions showing the desired characteristics for the compound of interest such as concentration of said compound or purity of said compound), are collected and removed from the process as product. In the processes depicted in FIGS. 2 to 7 at least one fraction of the eluate preceding the one or more first fraction(s) and/or at least one fraction of the eluate following the one or more first fraction(s) are re-loaded to the same chromatography matrix. This procedure can be repeated several times, and the process is typically continued until the volume of mixture comprising the product biomolecule (i.e. the total volume of feedstock) is exhausted.
Figure 3:
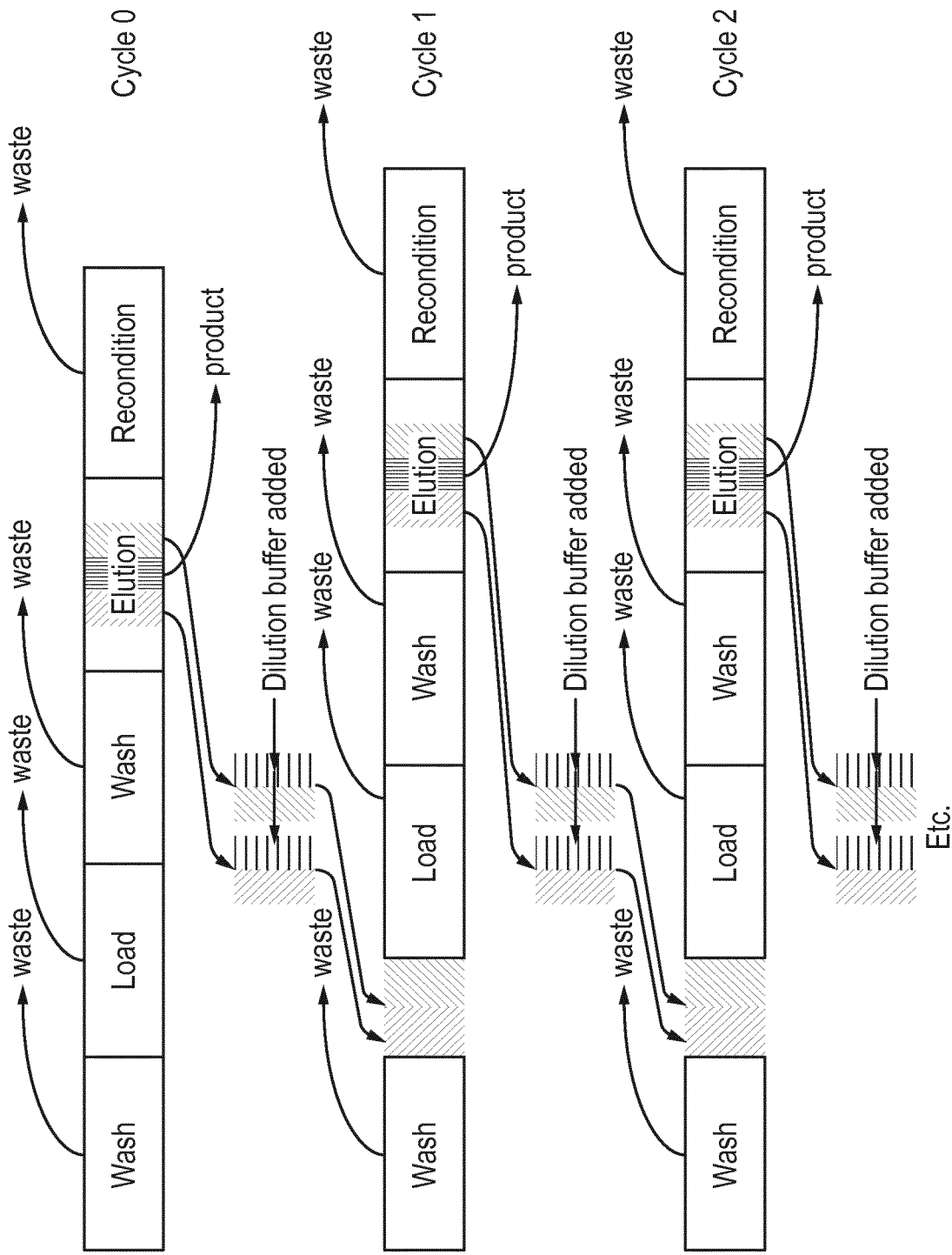
Figure 4:
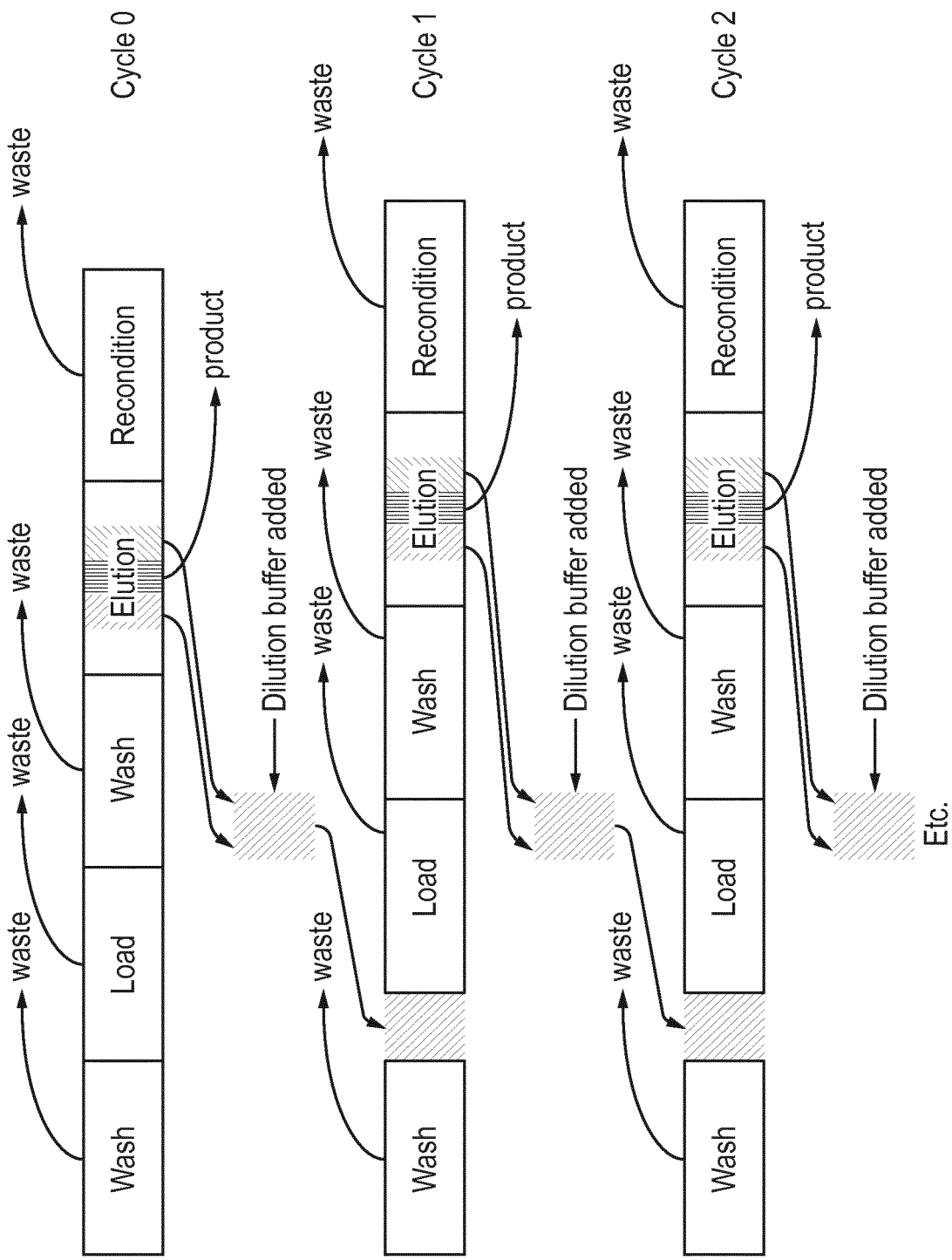
Figure 5:
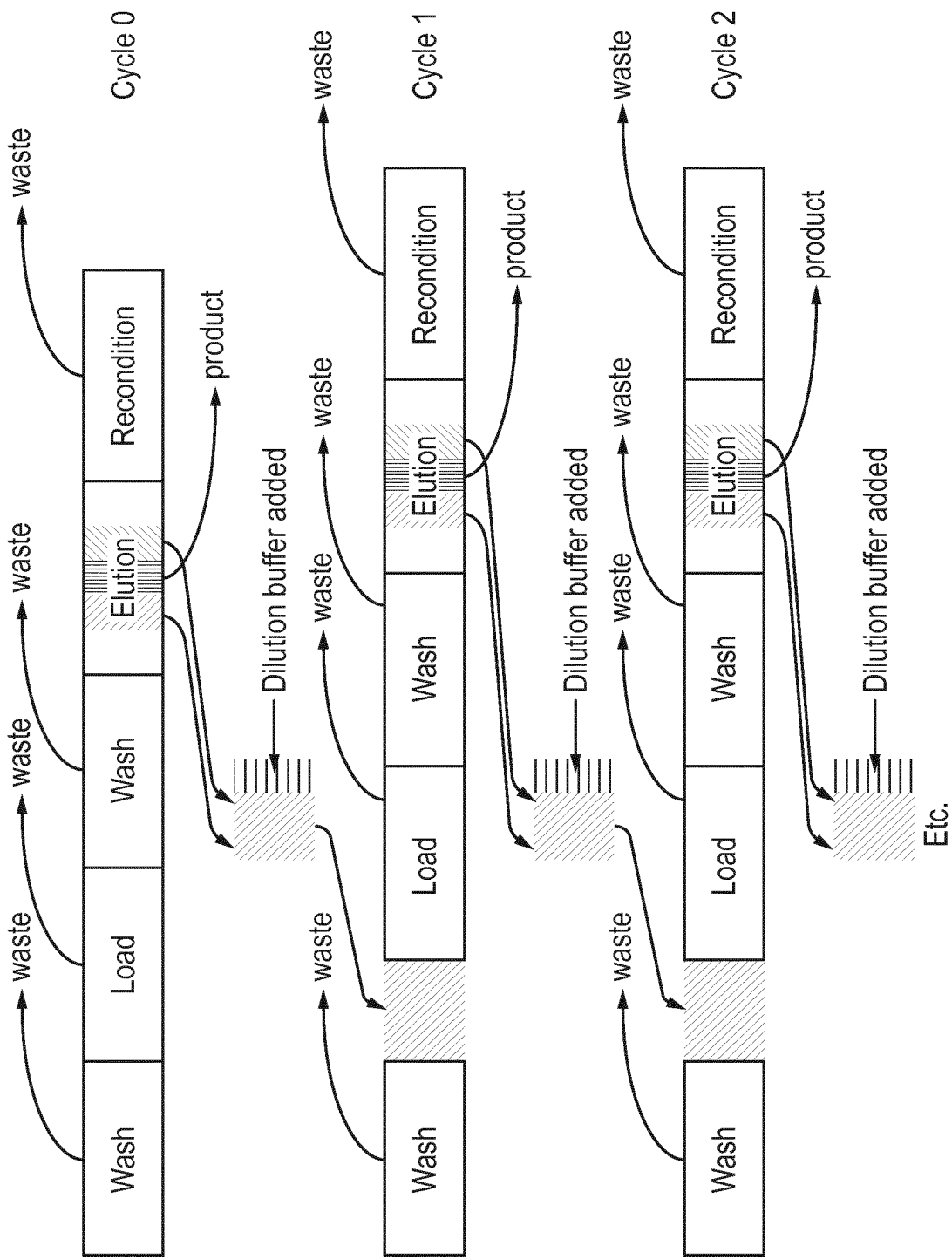

FIG. 5 shows a process very similar to the process shown in FIG. 4 except that the volume of the combined fraction of the eluate is significantly increased. The combined volume of the combined fraction may be increased e.g. by dilution. The dilution is an example of processing of the combined fraction prior to its reloading onto the matrix.

Figure 6:
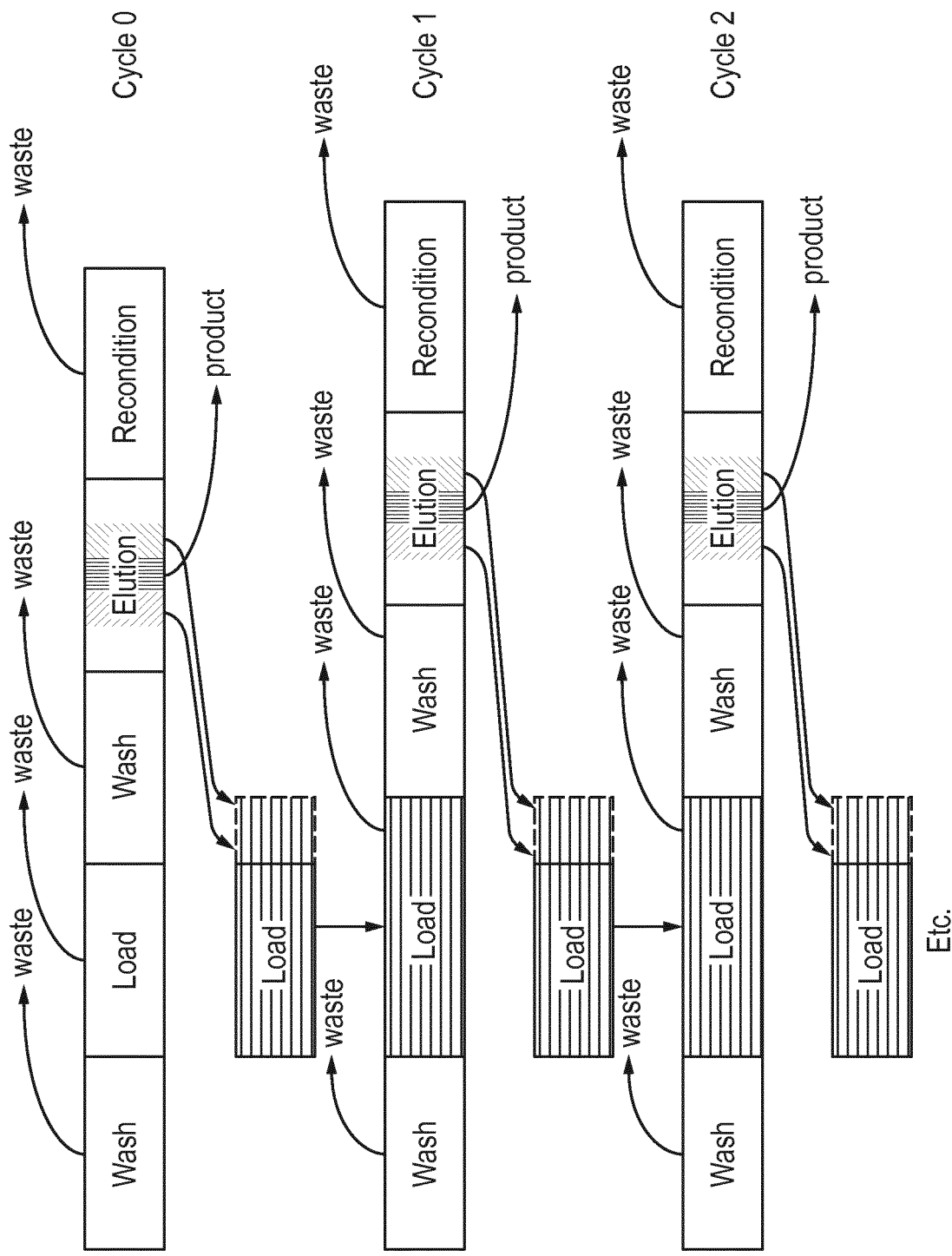

In the process shown in FIG. 6 the at least one preceding (leading) fraction and the at least one following (trailing) fraction are combined with further feed from the feedstock (i.e. with a further volume or with a further part of the volume of the mixture loaded in an operational chromatography cycle to the chromatography matrix), and applied to the chromatography matrix. Again, this procedure can be repeated several times. Although FIG. 6 depicts both trailing and leading fractions being reloaded those skilled in the art will appreciate that the method of the invention does not require both fractions to be so reloaded—e.g. only one of the trailing and/or leading fractions may be re-loaded onto the matrix.

Figure 7:
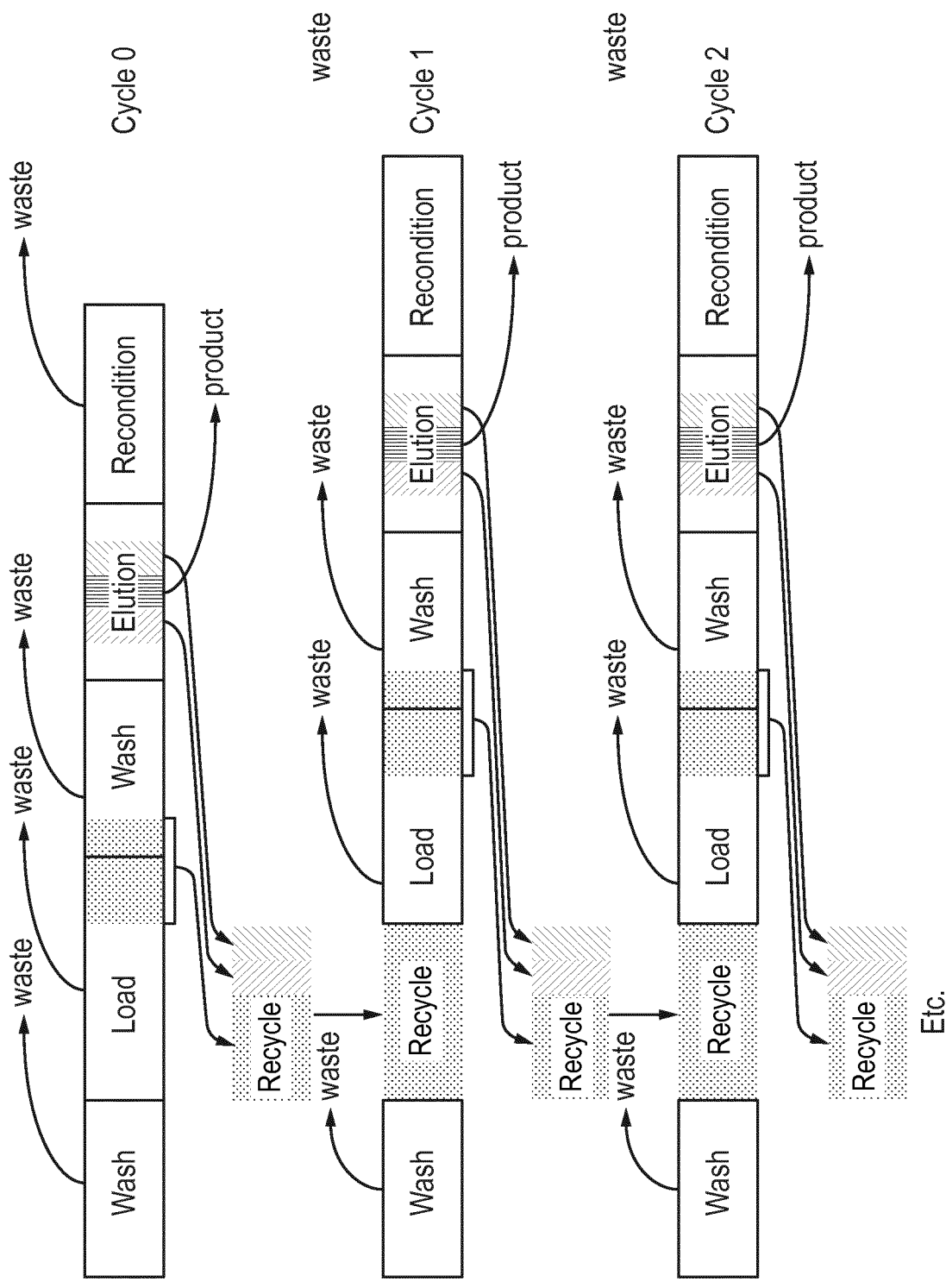

In the process shown in FIG. 7 the at least one preceding (leading) fraction and the at least one following (trailing) fraction are combined with a flow-through (referred to as "Recycle" in FIG. 7). Such flow-through is obtained when load containing the product biomolecule (compound of interest) is applied to the chromatography matrix until it leaks through. This figure thus depicts an example of excess load as described in more detail herein. Although FIG. 7 depicts both trailing and leading fractions being reloaded those skilled in the art will appreciate that the method of the invention does not require both fractions to be so reloaded—e.g. only one of the trailing and/or leading fractions may be re-loaded onto the matrix.

Figure 8:
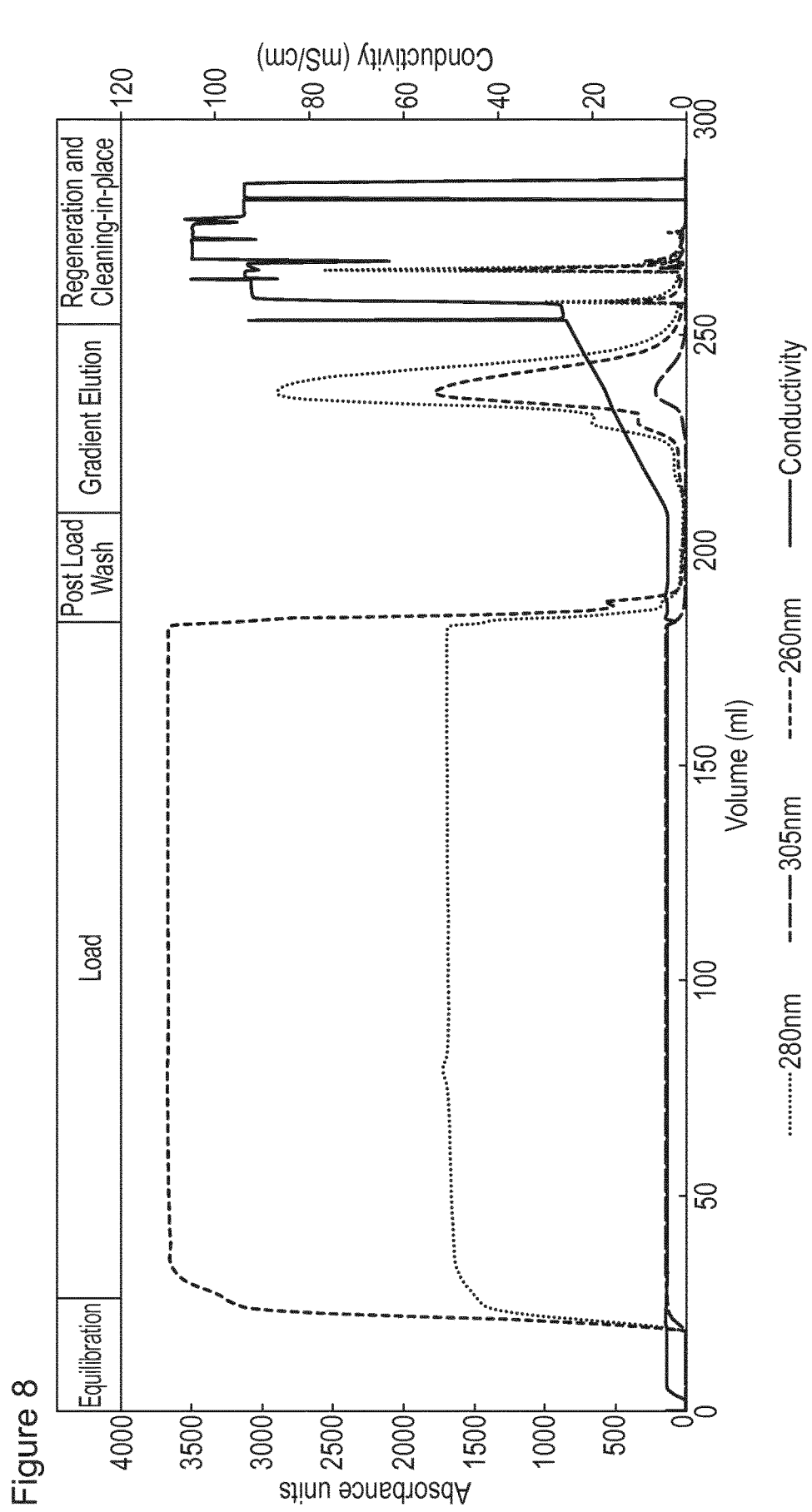
Figure 9:
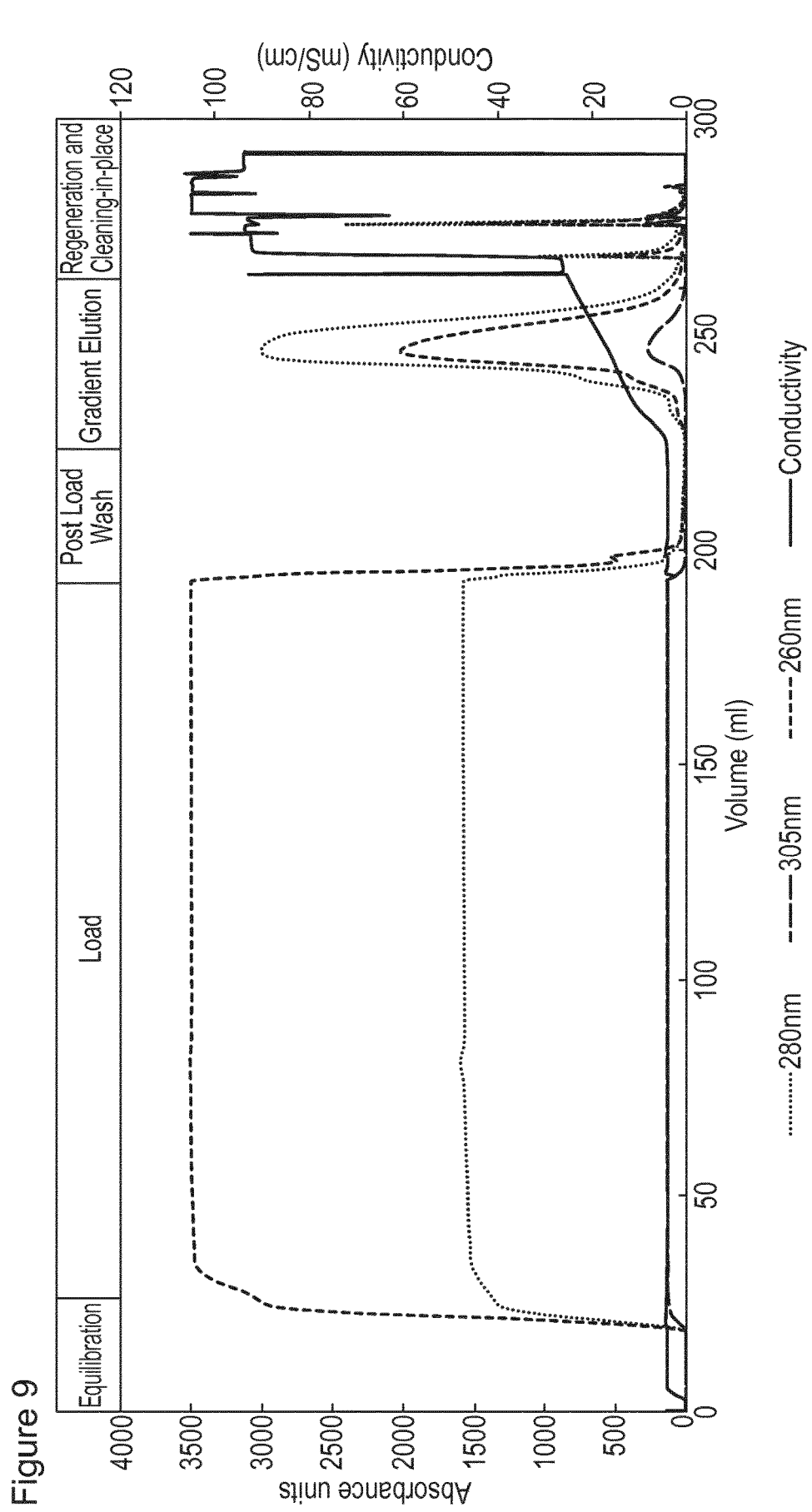
Figure 10:
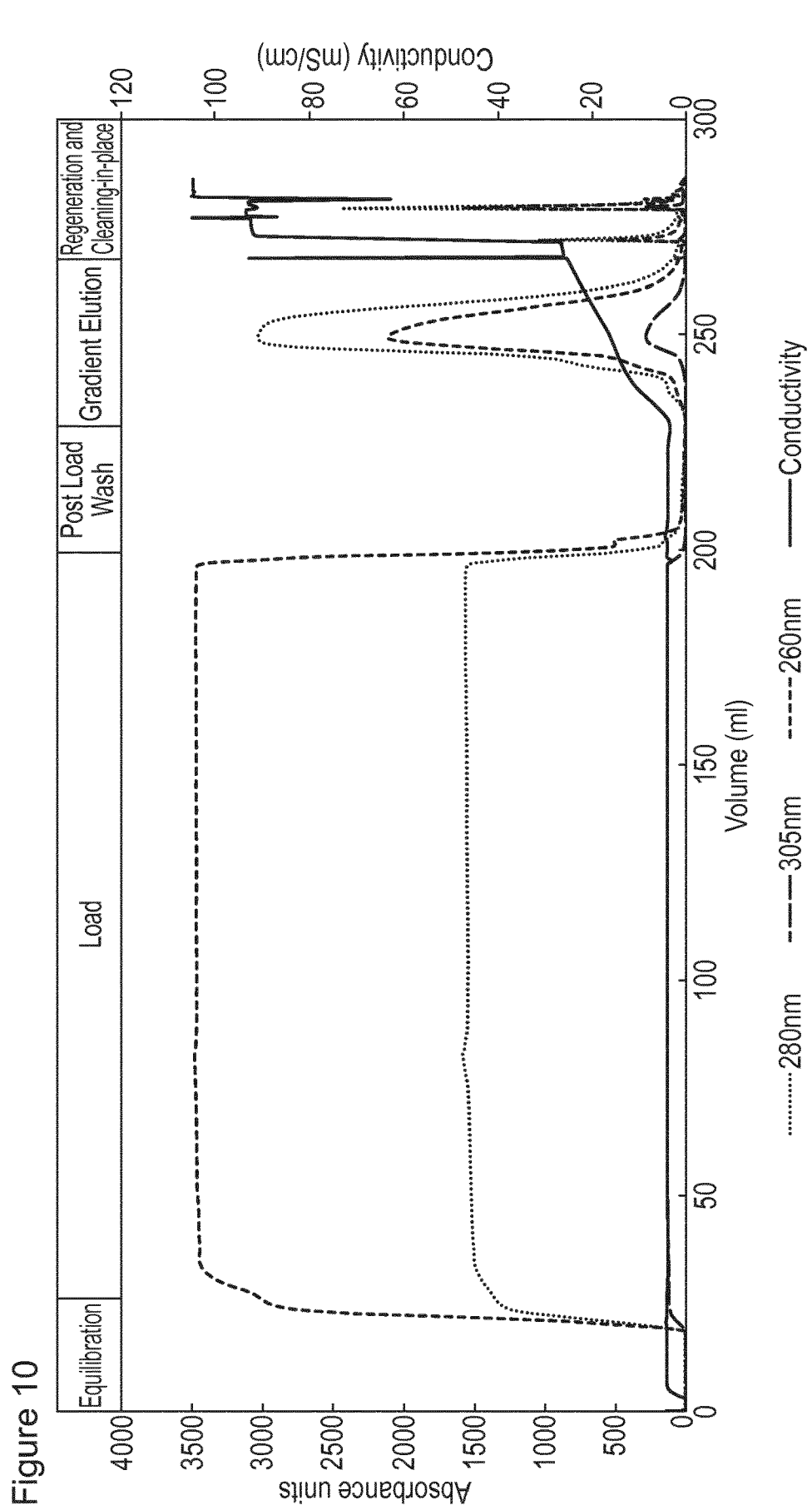
Figure 11:
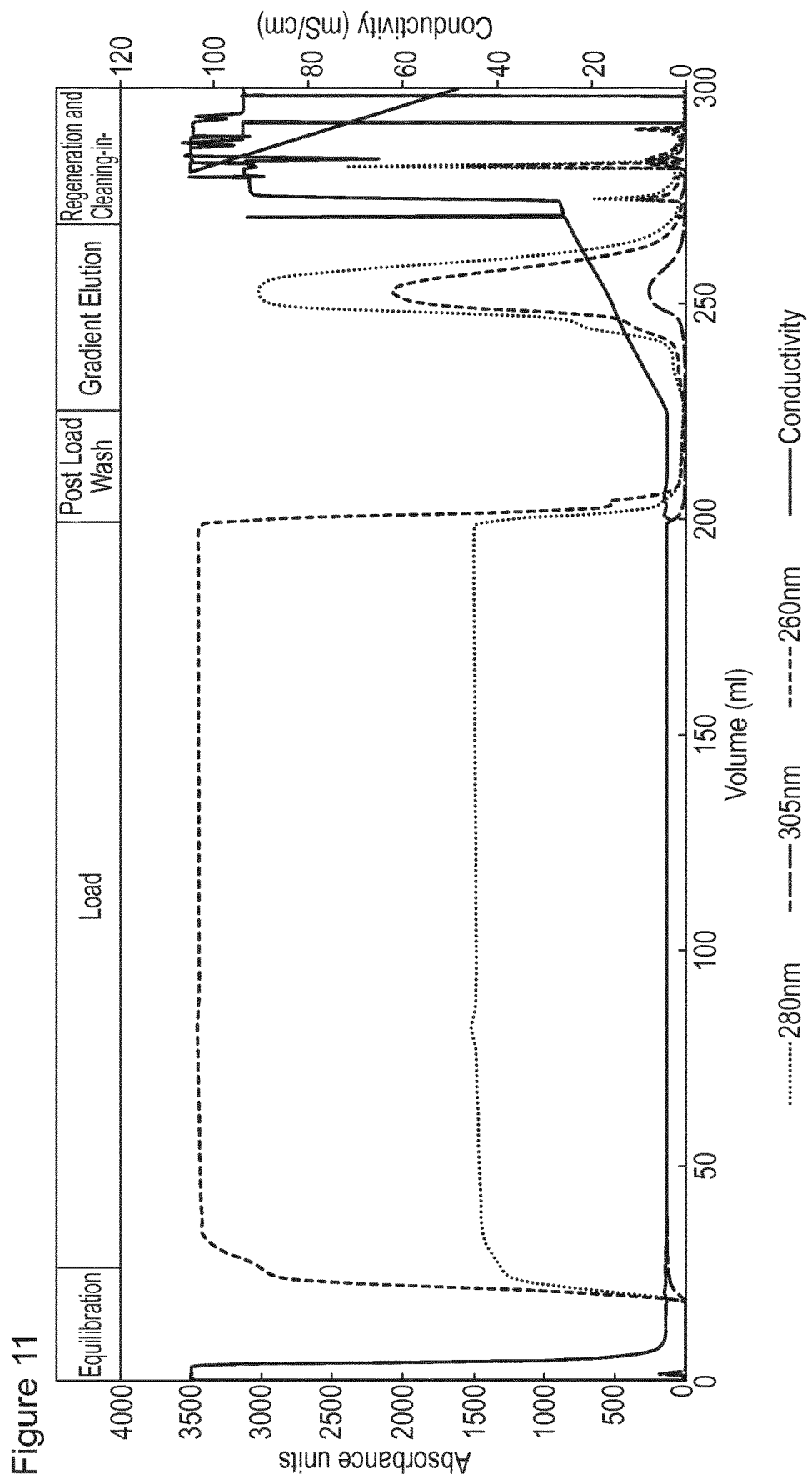
Figure 12:
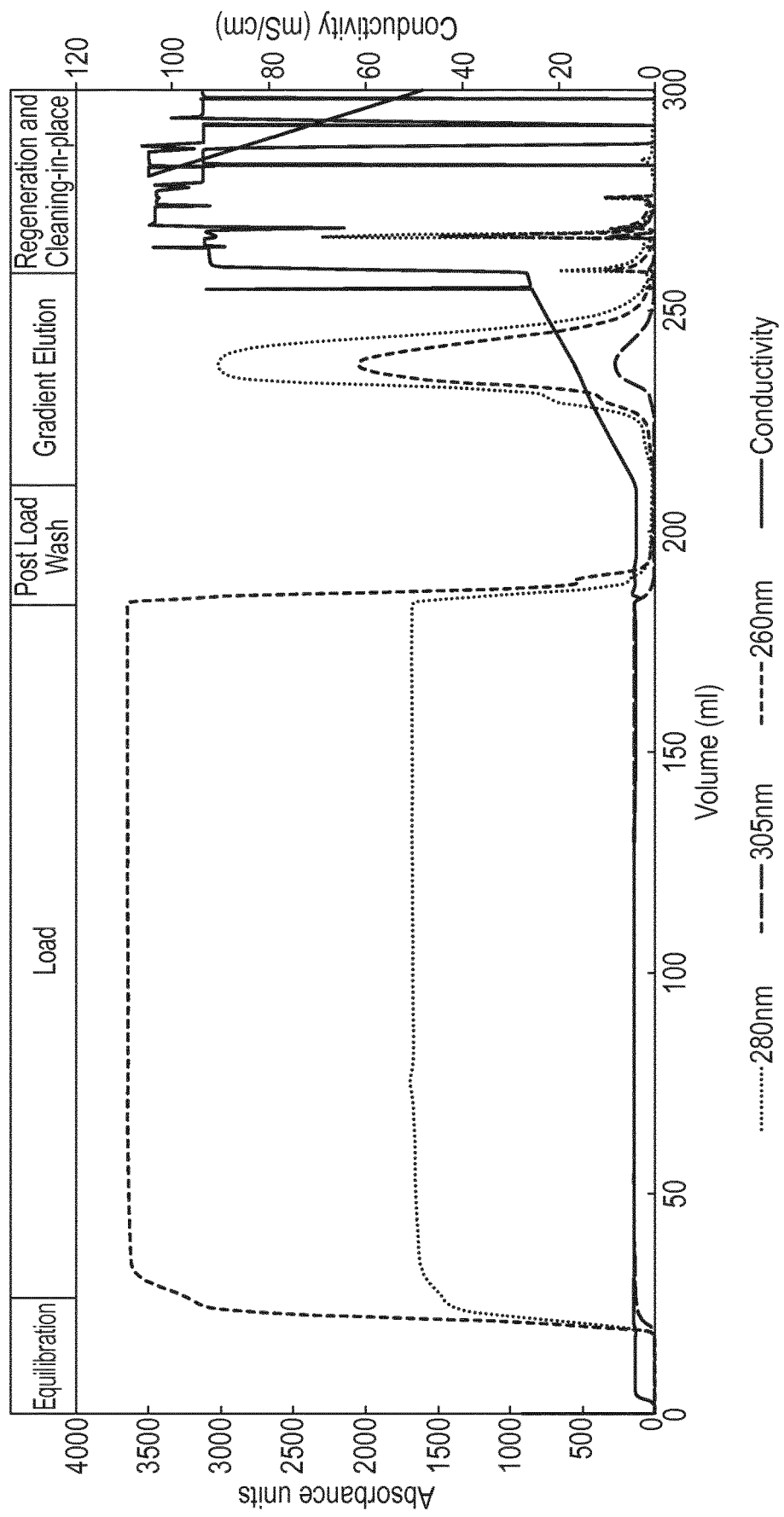
Figure 13:
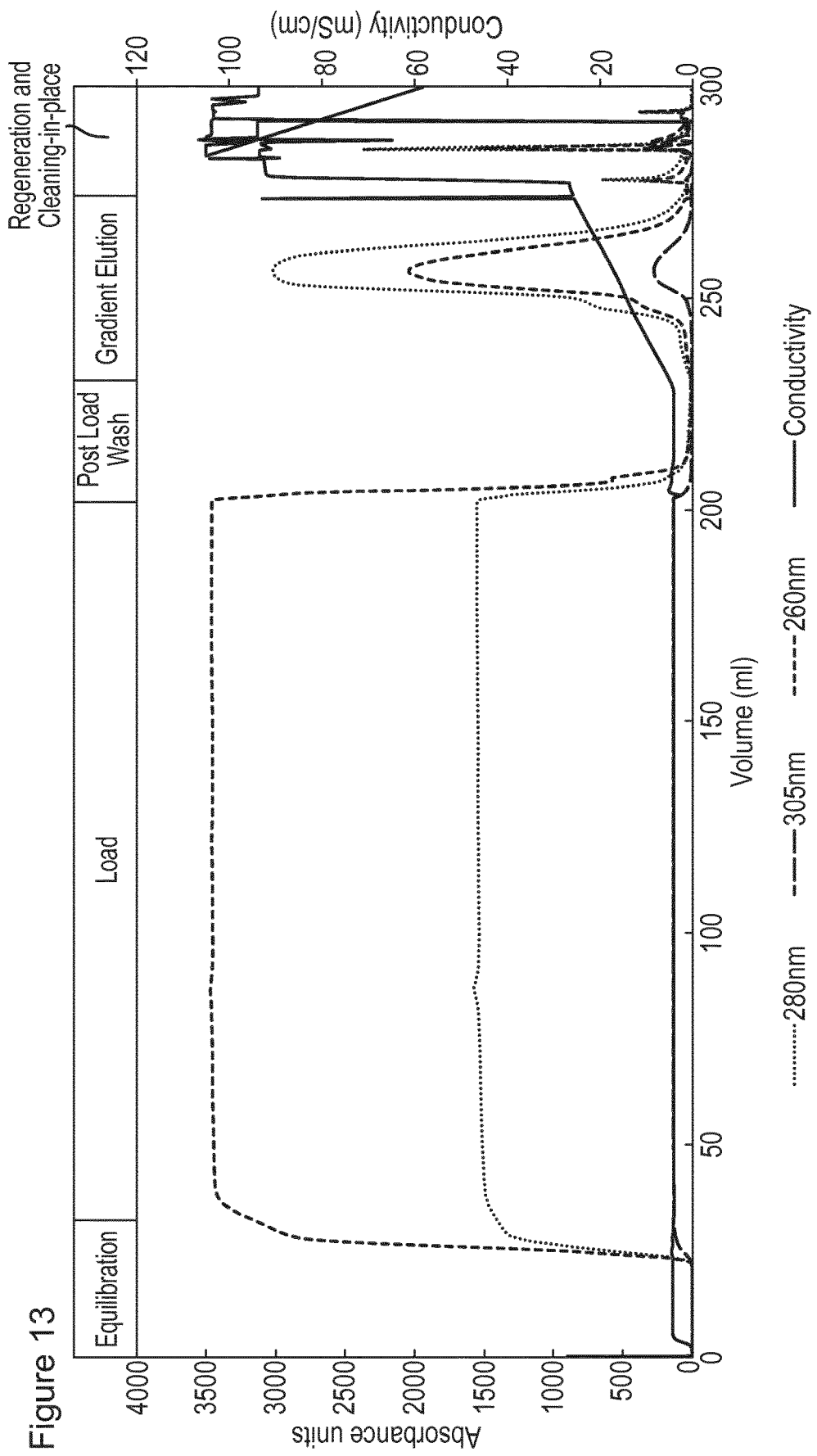
Figure 14:
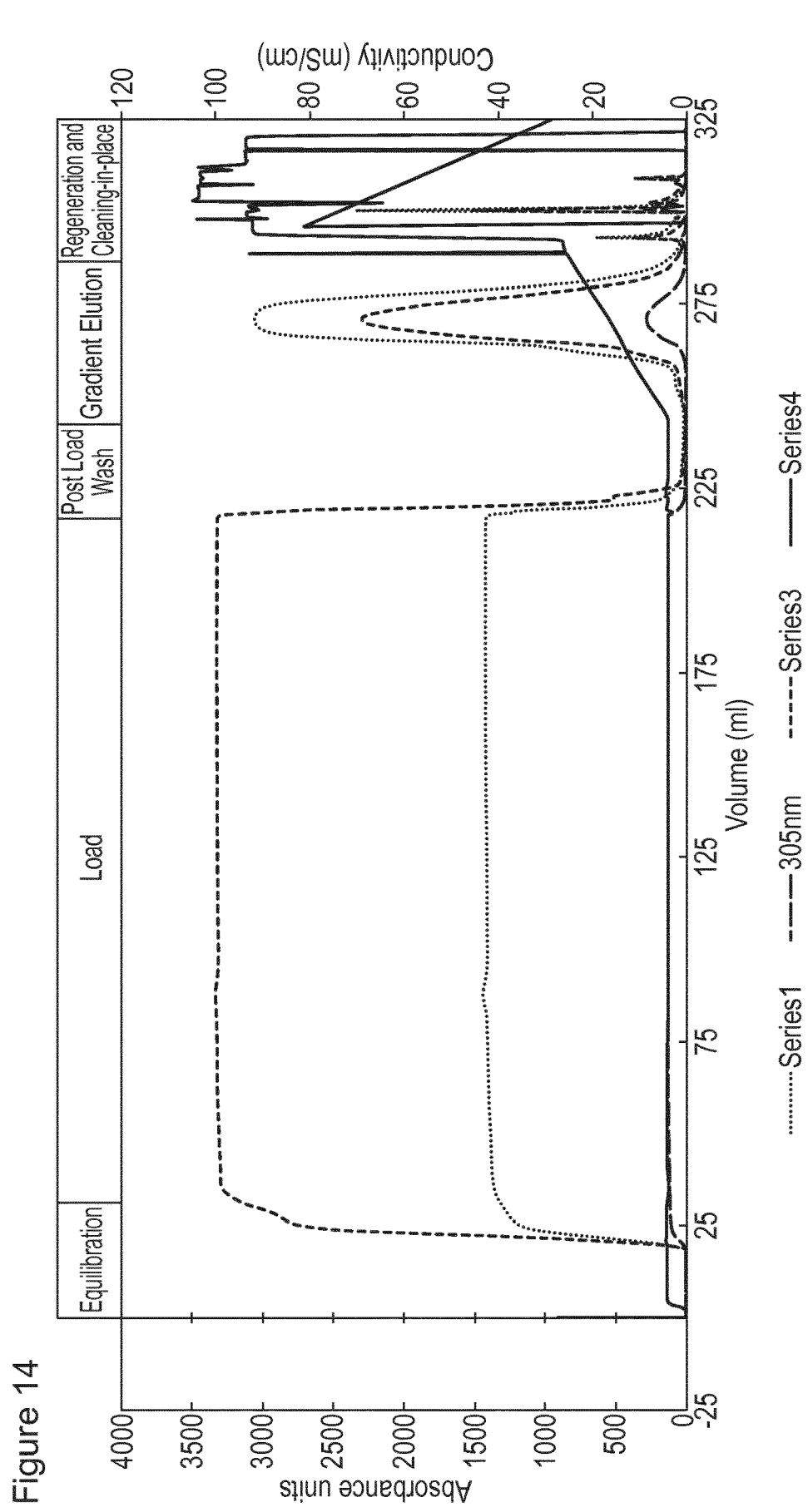

FIGS. 8 to 14 show chromatograms recorded during multiple cycles of a process according to the invention. FIGS. 8 to 14 provide an example of the processes of the invention comprising 7 operational cycles (i.e., with reference to the process of claim 1, steps (b), (c) and (d) are repeated 5 times). FIGS. 8 to 14 show the reproducibility of multiple cycles and demonstrate that compound of interest (e.g. product biomolecule) can be reproducibly obtained in high yield using the methods of the invention. FIG. 8 shows an initial stage of equilibration of the chromatography matrix followed by a load stage (step (a) of the processes of the invention). After loading is complete, the matrix may be washed and then the compound of interest (the product biomolecule) eluted from the matrix e.g. in a gradient elution (step (b) of the process). The peak recorded at 260 nm, 280 nm and 305 nm indicates elution of protein from the matrix. FIGS. 9 to 14 show subsequent cycles of the processes of the invention. In FIGS. 9 to 14, the load stage corresponds to step (d) of the processes of the invention. Accordingly, FIG. 8 shows a chromatogram of cycle 1 of the Example. FIG. 9 shows a chromatogram of cycle 2 of the Example. FIG. 10 shows a chromatogram of cycle 3 of the Example. FIG. 11 shows a chromatogram of cycle 4 of the Example. FIG. 12 shows a chromatogram of cycle 5 of the Example. FIG. 13 shows a chromatogram of cycle 6 of the Example. FIG. 14 shows a chromatogram of cycle 7 of the Example.

Figure 15:
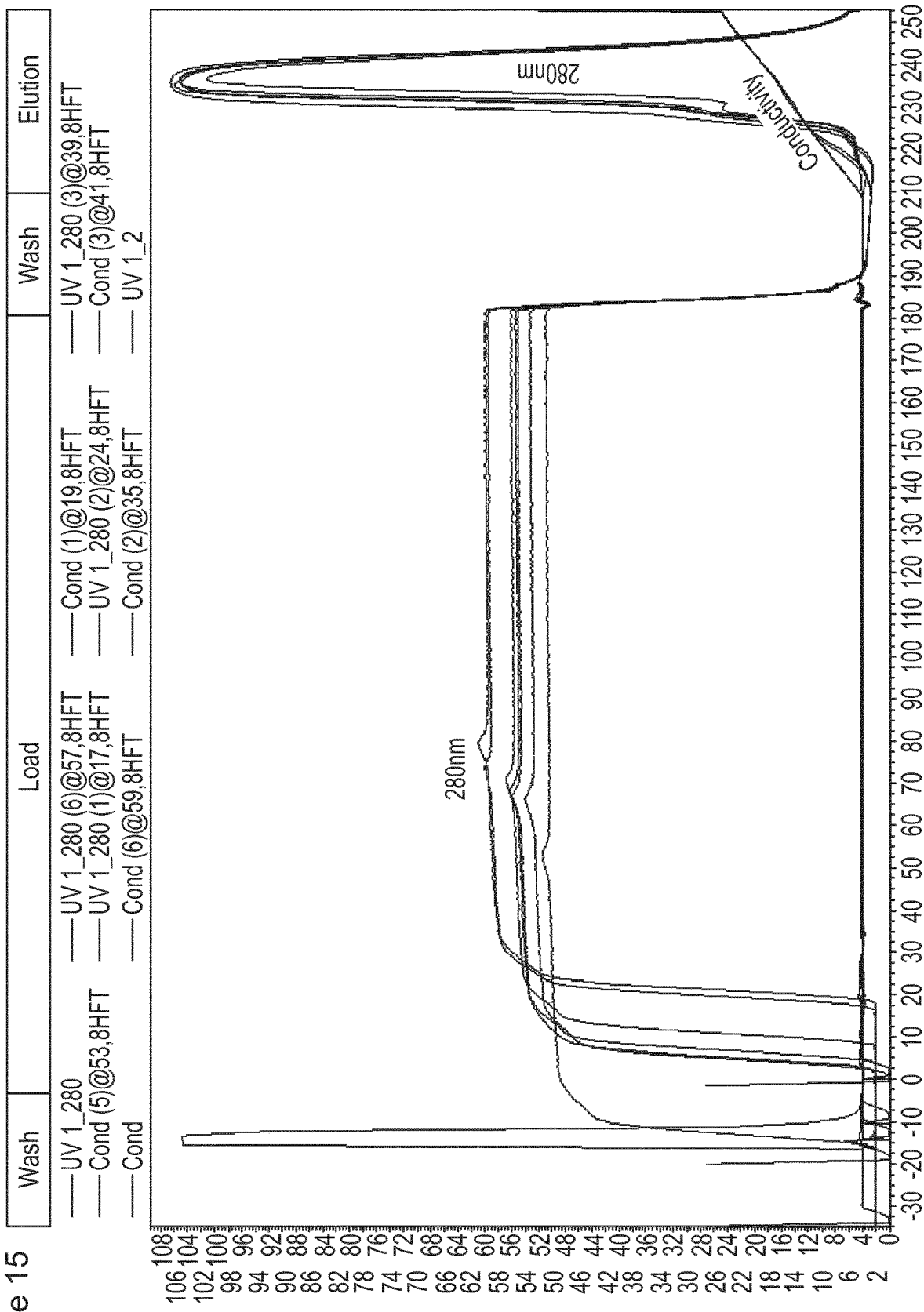

FIG. 15 shows an overlay of the chromatograms of cycles 1 to 7. FIG. 15 illustrates the high yield of target biomolecule from the processes according to the invention.

Figure 16:
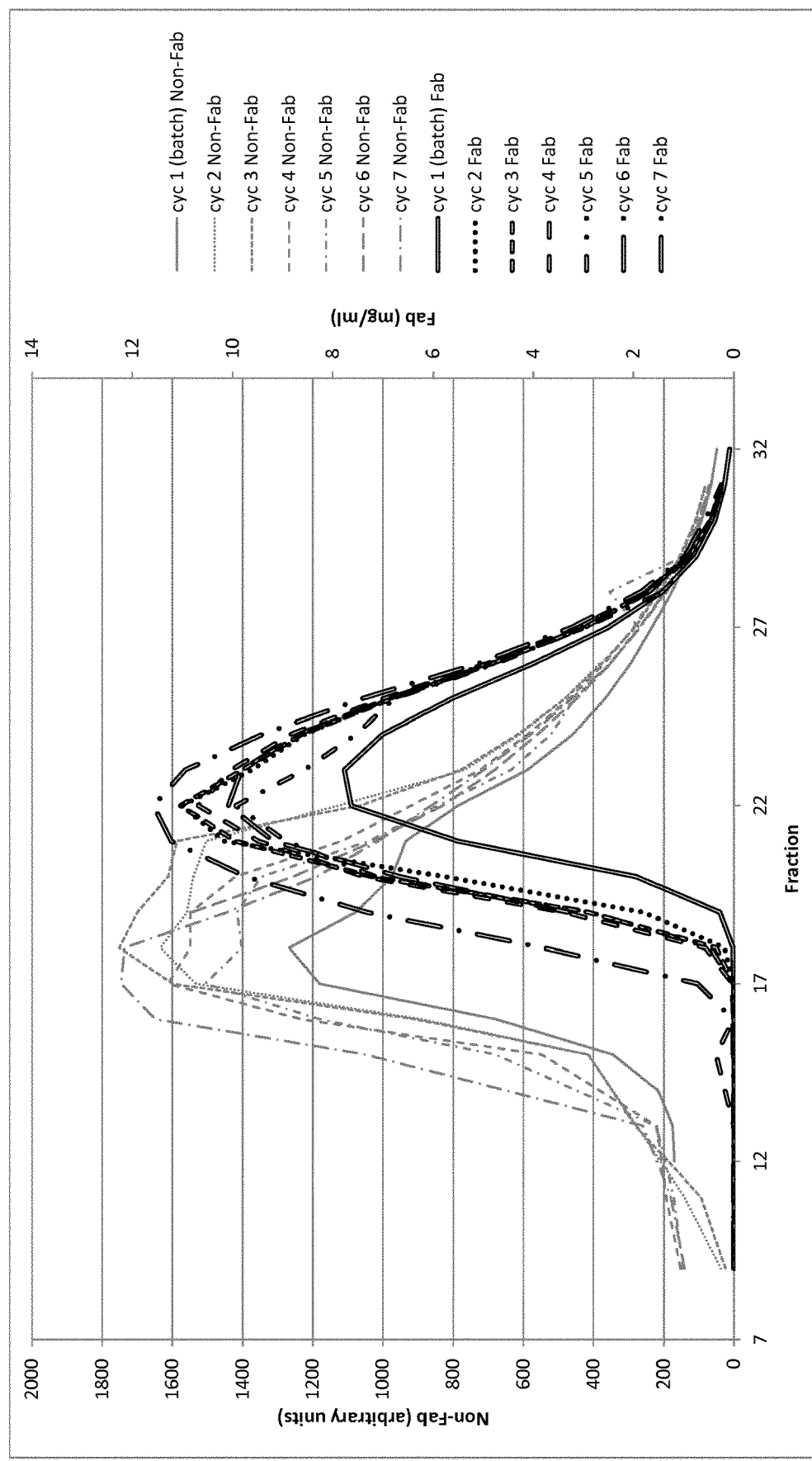
Figure 20:
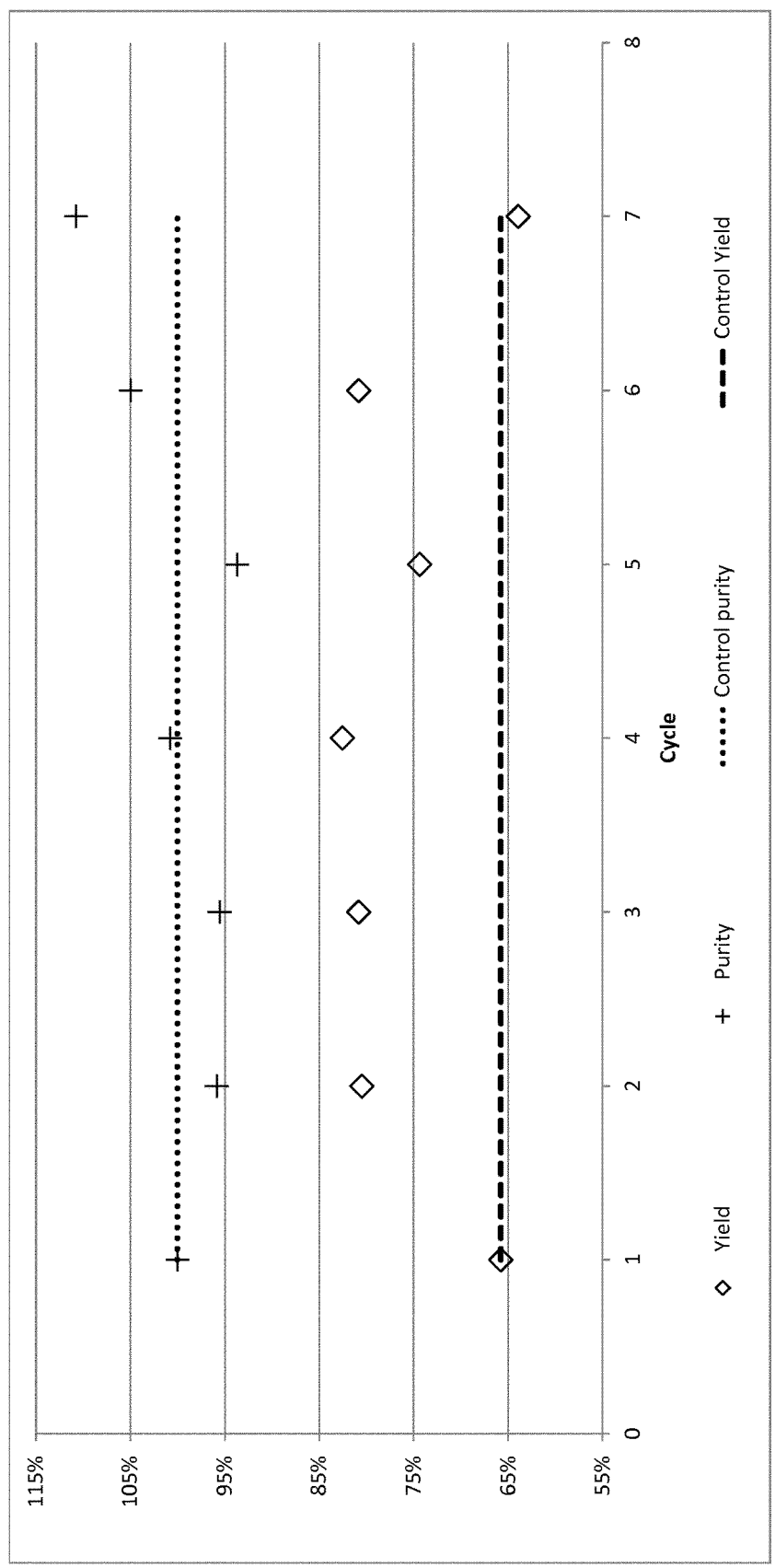

FIG. 16 is a diagram illustrating conflated impurity and Fab peaks in CEX gradient elution determined by Protein G HPLC. FIG. 17 is a table summarizing assayed quantities of Fab in retained pools (Assayed quantities in retained pools (Fractions 9-20 containing predominantly non-Fab and Fractions 23-31 containing predominantly Fab of interest). FIG. 18 is a table summarizing % yield gain in late cation exchange peak retained pool. FIG. 19 is a table summarizing % purity gain in late cation exchange peak retained pool. (Note that for FIGS. 17-19 Cycle 7 has a different range of included fractions—1-8 for the early peaks and 24-31 for the late peak). FIG. 20 is a diagram showing yield and purity gains in late cation exchange peak over cycles with baselines. (Note that since volumes are constant in each fraction, increases in total yield therefore also equate to increases in overall concentration.) The experiments giving rise to this data and the data summarized in FIGS. 17 to 20 are described in the Example.

DETAILED DESCRIPTION OF THE INVENTION

Many purification methods for proteins known in the art contain steps requiring the application e.g. of low or high pH, high salt concentration or other extreme conditions that may irreversibly jeopardize the biological activity of the protein to be purified and are therefore not suitable. Thus, separation of the desired protein to sufficient purity poses a formidable challenge. Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Antibodies and antibody fragments are of increasing importance in a range of therapeutic areas. One of the most important methods of producing antibodies and antibody fragments is by recombinant technology. Such techniques use a host cell to express the desired antibody, which is then separated from the production medium and purified.

Antibodies require glycosylation and are therefore generally expressed in eukaryotic expression systems employing eukaryotic cells, in particular mammalian cells such as CHO, PER.C6, NS0, BHK or Sp2/0 cells. In eukaryotic expression systems the protein of interest expressed such as an antibody is generally secreted into the cell culture medium. The medium can subsequently be separated easily from the protein secreting cells, e.g. by centrifugation or filtration. The protein of interest typically requires further purification, for example by chromatography.

Chromatography matrices used for the various chromatography techniques, particularly for large, industrial scale purification processes, are very expensive. They are generally reused following cleaning. Due to the harsh nature of the cleaning agents used, chromatography matrix efficiency decreases over time. Typically, chromatography matrices are not used very efficiently in the art, for example as their full maximum protein binding capacity is not exploited. In the art chromatography matrices are used such that they are loaded with protein of interest below their full capacity to improve yields. When protein matrices are loaded with protein of interest to their full capacity a lot of protein of interest is lost in the flow-through. Due to the high costs and the limited lifetime of chromatography matrices there is a need in the art for processes which optimally use a chromatography matrix.

Crude protein preparations from large scale cell culture processes typically cannot be purified in a single purification cycle. Due to the amount of protein to be purified several cycles of the same purification process are required to purify the output of the cell culture. The protein mixture to be purified is therefore frequently purified batch by batch in multiple purification cycles involving also multiple chromatography cycles. Continuous processes have also been implemented in large scale manufacturing processes for biopharmaceuticals. In continuous chromatography, several identical columns are connected in an arrangement that allows columns to be operated in series and/or in parallel, depending on the method requirements. Compared to single column or batch chromatography, wherein a single chromatography cycle is based on several consecutive steps, such as loading, wash, elution and regeneration, in continuous chromatography based on multiple identical columns all these steps occur simultaneously but on different columns each. Continuous chromatography operation results in a better utilization of chromatography resin, reduced processing time and reduced buffer requirements, all of which benefits process economy. A specific way of operating continuous chromatography is called simulated moving bed (SMB) chromatography. In simulated moving bed chromatography all the chromatography columns comprising the system are periodically and simultaneously moved in the direction opposite to the sample flow. The movement of the columns is realized by appropriate redirections of inlet and outlet stream to/from the columns which requires a sophisticated setup. Accordingly, continuous chromatography processes such as SMB processes are associated with significant complexities.

A semi-continuous chromatography process has been described in the art whereby rather than a single large chromatography column multiple smaller columns were used in row and loaded to a higher binding capacity. The flow-through of each column was directly loaded onto the following column. Alternatively, the flow-through of the first column was directed back to the first container harboring a mixture with protein of interest and then re-loaded onto the first column (Mahajan, George et al. 2012). The columns used were of very small laboratory scale and the authors concluded that the continuous mode chromatography using multiple columns offered advantages of reduced processing time.

Using several chromatography columns in row requires sophisticated flow control apparatus and control software, as well as additional chromatography hardware including pumps, valves, detectors and housing for each additional column, which add cost, increase the probability of part failure, increase the complexity of validation processes and complicate diagnosis of errors. Furthermore, in order to align the flow-through from one column to the correct period in the sequence for the adjoined receiving column, delay periods must be introduced such that they match, which reduces the operational speed. Since each additional receiving column must be started and stopped in staggered sequence resulting in columns that are inactive during these periods, an additional productivity penalty is incurred each time the operation is shut down or restarted.

There is thus a need for simple, efficient and cost effective processes for purification of proteins e.g. antibodies involving the use of chromatography matrices. The methods of the invention are intended to address this need.

Processes of the Invention

The problem underlying the present invention is solved by the methods provided herein.

The invention provides an industrial-scale process for the purification of a product biomolecule from a feedstock comprising the product biomolecule and at least one impurity, the process comprising the steps of:

a) loading feed from the feedstock to a chromatography matrix such that the product biomolecule binds to the chromatography matrix;

b) eluting the product biomolecule from the chromatography matrix in an eluate by applying an elution solution to the chromatography matrix;
wherein the eluate comprises:
a first fraction comprising purified product biomolecule; and
a second fraction comprising both the product biomolecule and at least one impurity, the second fraction comprising one or more leading and/or trailing fraction(s);
and wherein the first fraction is collected separately from the second fraction;

c) holding the second fraction in one or more container(s);

d) loading the second fraction from the container(s) and additional feed from the feedstock to the chromatography matrix such that the product biomolecule in the second fraction binds to the chromatography matrix; wherein the additional feed is loaded simultaneously with or sequentially to the second fraction; and e) eluting the product biomolecule from the chromatography matrix in an eluate by applying an elution solution to the chromatography matrix, wherein the eluate comprises purified product biomolecule;

wherein the chromatography matrix in step (a), step (b), step (d) and step (e) is the same chromatography matrix.

As explained in more detail below, step (d) comprises loading additional feed from the feedstock to the chromatography matrix simultaneously with or sequentially to the second fraction.

Preferably, in the process of the invention, steps (b), (c) and (d) are repeated. Preferably, steps (b), (c) and (d) are performed at least twice, more preferably at least three times, e.g. at least four times, such as at least five times, e.g. at least 10 times or more. Those skilled in the art will be readily able to select an appropriate number of times to repeat these steps according to the volume of feedstock, the purity of the product biomolecule in the feedstock, the characteristics of impurities present in the feedstock; etc.

It will be apparent that when steps (b), (c) and (d) are repeated once, the process comprises three loading/elution cycles (i.e. a first load cycle in step (a); a first elution cycle in step (b); a second load cycle in step (d); a second elution cycle in a second step (b); a third load cycle in a second step (d) and a third elution cycle in step (e)). When steps (b), (c) and (d) are repeated twice, then the processes of the invention comprise four loading/elution cycles (i.e. a first load cycle in step (a); a first elution cycle in step (b); a second load cycle in step (d); a second elution cycle in a second step (b); a third load cycle in a second step (d); a third elution cycle in a third step (b); a fourth load cycle in a third step (d) and a fourth elution cycle in step (e)). In other words, when steps (b), (c) and (d) are repeated n times (wherein n is a positive integer), the process comprises (n+2) loading/elution cycles.

Preferably, steps (a) and (b) are repeated multiple times. Accordingly, feed from the feedstock may be applied to the chromatography matrix in multiple volumes and first and second fractions eluted from the chromatography matrix following each loading of feed. The second fractions collected may preferably be pooled together. Step (c) preferably involves holding the pooled second fractions in the one or more container(s).

Alternatively, the second fractions obtained following each repeat of steps (a) and (b) may be separately held in one or more container(s). The second fractions may then be reloaded either as a single volume or as multiple volumes onto the chromatography matrix such that the product biomolecule in the second fraction binds to the chromatography matrix. Preferably, therefore, steps (a) and (b) are repeated multiple times; the second fractions collected in each step (b) are pooled together; step (c) comprises holding the pooled second fractions in the container(s); and step (d) comprises loading the pooled second fractions from the container(s) to the chromatography matrix such that the product biomolecule in the pooled second fractions binds to the chromatography matrix.

In a second aspect, provided is a process for the purification of a compound of interest from a mixture comprising the compound of interest, wherein the process comprises the steps of a) in a first operational chromatography cycle loading a mixture comprising the compound of interest from a first container to a chromatography matrix operated such that the compound binds to the chromatography matrix;

b) eluting the compound of interest from the chromatography matrix and collecting the eluate containing the compound of interest as fractions of the eluate;

c) re-loading one or more of the fractions of the eluate to the same chromatography matrix operated such that the compound of interest binds to the chromatography matrix.

In the second aspect, preferably, the re-loading of step c) is re-loading in a further operational chromatography cycle one or more of the fractions of the eluate to the same chromatography matrix operated such that the compound of interest binds to the chromatography matrix. In accordance therewith, the process of the second aspect may therefore comprise the steps of:

a) in a first operational chromatography cycle loading a mixture comprising the compound of interest from a first container to a chromatography matrix operated such that the compound binds to the chromatography matrix;

b) eluting the compound of interest from the chromatography matrix and collecting the eluate containing the compound of interest as fractions of the eluate;

c) re-loading in a further chromatography cycle one or more of the fractions of the eluate to the same chromatography matrix operated such that the compound of interest binds to the chromatography matrix.

Preferably, in the second aspect, the further operational chromatography cycle is the chromatography cycle immediately following.

Alternatively, in another embodiment of the second aspect, the re-loading of step c) is re-loading in the same operational chromatography cycle one or more of the fractions of the eluate to the same chromatography matrix operated such that the compound of interest binds to the chromatography matrix. In accordance therewith, the process may therefore comprise the steps of:

a) in a first operational chromatography cycle loading a mixture comprising the compound of interest from a first container to a chromatography matrix operated such that the compound binds to the chromatography matrix;

b) eluting the compound of interest from the chromatography matrix and collecting the eluate containing the compound of interest as fractions of the eluate;

c) re-loading in the same chromatography cycle one or more of the fractions of the eluate to the same chromatography matrix, i.e. the first operational chromatography cycle operated such that the compound of interest binds to the chromatography matrix.

Preferably, the compound of interest is a product biomolecule as defined herein.

It will be apparent from the above discussion that the methods of the invention involve loading a feedstock (i.e. a mixture comprising the compound of interest, i.e. the product biomolecule) to a matrix; eluting the product biomolecule (the compound of interest) from the matrix; collecting "first fractions" which comprise purified product biomolecule (i.e. fractions having a desired characteristic) and "second fractions" which comprise product biomolecule and at least one impurity (i.e. fractions which do not have a desired characteristic); and reloading one or more of such second fractions to the same chromatography matrix. These and other aspects of the invention are described in detail below.

Retained Fractions

As described above, the processes of the invention involve loading a feed from a feedstock onto a chromatography matrix and eluting the compound of interest, i.e. the product biomolecule from the matrix. The eluate thus comprises one or more "first fractions" which comprise purified product biomolecule. The eulate also comprises one or more "second fractions" which comprise product biomolecule and at least one impurity.

The first fraction(s) are also referred to herein as "fractions having a desired characteristic", or "fractions of the eluate which are not re-loaded to the same chromatography matrix". The second fractions are also referred to herein as "fractions having an undesired characteristic", or "fractions of the eluate re-loaded to the same chromatography matrix".

Those skilled in the art will be readily able to identify the fractions of the eluate to be (re)-loaded to the chromatography matrix in step (d) of the processes of the invention and distinguish such fractions from fractions comprising purified product biomolecule. Any suitable means can be used to determine the identify the fractions of the eluate to be (re)-loaded to the chromatography matrix in step (d) of the processes of the invention. For example, the fractions to be (re)-loaded can be identified by determining the volume of eluate obtained or the run time of the method (i.e. based on pre-learned knowledge of the nature of the feedstock and the characteristics of the first and second fractions). Alternatively, the fractions to be (re)-loaded can be identified based on measurements taken during the course of the method. For example, the first fractions preferably have a minimum concentration of the product biomolecule (the compound of interest) and/or a maximum concentration of compounds other than the product biomolecule, i.e. impurities. Preferably, the first fractions have a minimum concentration of the product biomolecule (compound of interest).

In a similar manner, the second fractions which are to be (re)-loaded to the chromatography matrix in step (d) of the processes of the invention preferably have a maximum concentration of the compound of interest or product biomolecule and/or a minimum concentration of compounds other than the compound of interest, i.e. impurities. Preferably, the second fractions have a minimum concentration of compounds other than the compound of interest (impurities).

The concentration of protein or any other molecule of interest in the one or more of the fractions of the eluate and/or in the flow-through (see below) can be measured in the processes of the invention by any technique known in the art such as but not limited to measuring the optical absorbance or fluorescence.

A compound of interest and particularly a protein of interest can be determined in a sample (e.g. in a first fraction, a second fraction and/or the flow-through) in the processes of the invention by observing increases or decreases in the time course of the ultraviolet absorbance or fluorescence signal beyond the steady-state level of background ultraviolet absorbance or fluorescence signal caused by other protein impurities in the sample.

The concentration of a compound of interest and particularly a protein of interest in a sample (e.g. in a first fraction, a second fraction and/or the flow-through) can be measured in the processes of the invention by ultraviolet absorbance or fluorescence at any suitable wavelength as known in the art, e.g. at 280 nm, and preferably using at a sub-optimal excitation and/or emission wavelength, such as 290 nm, 300 nm or 310 nm, to allow for detection of the protein of interest in the sample when there is signal in excess from protein impurities in the sample.

The concentration of the compound of interest in a sample may be determined on-line, at-line or offline. Determining the concentration online means that the concentration is determined in the process of the invention, e.g. with a detector connected to the outlet of the chromatography matrix or positioned at or in the container(s) in which said sample is collected in real time. Determining the concentration at-line means that the concentration is determined from a specimen taken from the outlet of the chromatography matrix or the container(s) in which said sample is collected. Determining the concentration offline means that the concentration is determined from a specimen taken from the outlet of the chromatography matrix or the container(s) in which said sample is collected and measured after a delay on a detector placed distant, i.e. in a separate room from the matrix. Preferably, the concentration of a sample is determined on-line or at-line, more preferably on-line.

Those skilled in the art will recognize that the concentration of impurities in a sample can be measured in the same way as that used to measure the concentration of product biomolecule in the sample.

Those skilled in the art will therefore appreciate that, in the invention, the first fraction(s) is different from the second fraction(s). The first fraction is collected separately from the second fraction. The first fraction is typically not (re)-loaded to the chromatography matrix, whereas the second fraction is (re)-loaded to the chromatography matrix for further purification. The first fraction comprises purified product biomolecule, whereas the second fraction(s) comprises product biomolecule and at least one impurity; i.e. the second fraction(s) does not comprise purified product biomolecule.

As used herein, the term "purified" product biomolecule does not necessarily require that the product biomolecule is 100% pure. The purified product biomolecule may contain no more than an acceptable level of impurities, providing that such level is lower than the level of impurities in the feedstock. The purified product biomolecule may be substantially free of impurities (e.g. at least 50% pure, such as at least 70% pure, more preferably at least 90% pure, e.g. at least 95% pure, at least 97% pure, preferably at least 98 or 99% pure, determined e.g. relative to all biomolecules in the fraction, e.g. by wt %). Impurities may comprise biomolecules other than the product biomolecule, or may comprise modified or degraded product biomolecule. Impurities present in the second fraction are typically different from any which may be present or retained in the first fraction.

In a similar manner, with particular reference to the second aspect discussed above, the one or more fractions of the eluate re-loaded to the same chromatography matrix is/are different from one or more fractions of the eluate having a desired characteristic. The one or more fractions of the eluate having a desired characteristic are not re-loaded to the same chromatography matrix. It is within the present invention that, as described further below, such not re-loaded fractions are either further processed by a method different from the chromatography treatment, or are ready for use. The number of the not re-loaded fractions will be determined by a person skilled in the art depending on the object underlying the chromatography treatment. For example, if a certain content or concentration of the compound of interest is reached in one or several of the fractions of the eluate, such one or several of the fractions will not be re-loaded to the same chromatography matrix. Another criterion for determining whether one or several of the one or more of the fractions of the eluate is to be re-loaded to the same chromatography matrix is the absence or decreased concentration of undesired compounds such as, for example, impurities.

Leading and Trailing Fractions

As described above, crude extracts of biomolecules typically contain impurities having similar binding characteristics to the chromatography matrix as the product biomolecule compound of interest). The elution profile of such impurities typically overlaps at least in part with the product biomolecule. Accordingly, "leading fractions" comprise both the product biomolecule (the compound of interest) and impurities which bind to the chromatography matrix less strongly than the product biomolecule. "Trailing fractions" comprise both the product biomolecule (the compound of interest) and impurities which bind to the chromatography matrix more strongly than the product biomolecule. Leading fractions elute from the chromatography matrix prior to the product biomolecule (the compound of interest); and trailing fractions elute from the chromatography matrix after the product biomolecule (the compound of interest). Leading fractions are also referred to as "preceding fractions". Trailing fractions are also referred to as "following fractions".

In the methods of the invention, the second fraction comprises one or more leading fraction(s) and/or one or more trailing fraction(s) as defined herein.

Preferably, the second fraction comprises or consists of one or more leading fraction(s). In other words, with particular reference to the second aspect, the one or more fractions of the eluate re-loaded to the same chromatography matrix is/are preferably at least one fraction of the eluate eluting from the chromatography matrix prior to the one or more fractions of the eluate having a desired characteristic. It is within the skills of a person of the art to determine the number of such one or more fractions of the eluate eluting from the chromatography matrix prior to the one or more fractions of the eluate having a desired characteristic as described in more detail herein. In other words, those skilled in the art will readily be able to identify suitable leading fractions for incorporating into the second fraction for use in the process of the invention. Parameters which can be used to identify suitable leading fractions for incorporating into the second fraction include a minimum concentration of the compound of interest or product biomolecule and/or a maximum concentration of compounds other than the compound of interest, i.e. impurities; which can be determined as described above.

Preferably, the second fraction preferably comprises or consists of the leading fraction immediately preceding the first fraction. In other words, the one or more fractions of the eluate different from one or more fractions of the eluate having a desired characteristic preferably comprise the fraction immediately eluting from the chromatography matrix prior to the one or more fractions of the eluate having a desired characteristic. Thus, the second fraction preferably comprises or consists of the fraction immediately neighbouring the first fraction and eluting from the chromatography matrix immediately before the first fraction. By including such fraction of the eluate the purification and/or enrichment of the compound of interest is particularly increased. For example, the leading fraction immediately preceding the first fraction typically contains higher concentrations of the compound of interest/the product biomolecule than leading fractions which further precede the first fraction. By retaining such leading fractions, the overall purification yield of the process is increased.

Preferably, the second fraction comprises or consists of a trailing fraction. In other words, with particular reference to the second aspect, the one or more fractions of the eluate re-loaded to the same chromatography matrix is/are preferably at least one fraction of the eluate eluting from the chromatography matrix after the one or more fractions of the eluate having a desired characteristic. As in the case when the second fraction comprises or consists of a leading fraction (described above), those skilled in the art will readily be able to identify suitable trailing fractions for incorporating into the second fraction for use in the process of the invention. Parameters which can be used to identify suitable trailing fractions for incorporating into the second fraction include a minimum concentration of the compound of interest or product biomolecule and/or a maximum concentration of compounds other than the compound of interest, i.e. impurities; which can be determined as described above.

Preferably, the second fraction comprises or consists of the trailing fraction immediately following the first fraction. In other words, the one or more fractions of the eluate different from one or more fractions having a desired characteristic preferably comprise the fraction immediately eluting from the chromatography matrix after the one or more fractions of the eluate having a desired characteristic. Thus, the second fraction preferably comprises or consists of the fraction immediately neighbouring the first fraction and eluting from the chromatography matrix immediately after the first fraction. As in case of re-loading the fraction of the eluate eluting immediately prior to the one or more fractions of the eluate having a desired characteristic, including such fraction of the eluate specifically increases the purification and/or enrichment of the compound of interest. For example, the trailing fraction immediately following the first fraction typically contains higher concentrations of the compound of interest/the product biomolecule than trailing fractions which further follow the first fraction. By retaining such trailing fractions, the overall purification yield of the process is increased.

Preferably, the second fraction comprises or consists of both the leading fraction immediately preceding the first fraction and the trailing fraction immediately following the first fraction. In other words, with particular reference to the second aspect, the one or more fractions of the eluate different from one or more fractions having a desired characteristic and thus the one or more fraction to be re-loaded to the same chromatography matrix comprise the fraction immediately eluting from the chromatography matrix prior to the one or more fractions of the eluate having a desired characteristic and the fraction immediately eluting from the chromatography matrix after the one or more fractions of the eluate having a desired characteristic. Thus, the second fraction preferably comprises or consists of the fraction immediately neighbouring the first fraction and eluting from the chromatography matrix immediately before the first fraction, and the fraction immediately neighbouring the first fraction and eluting from the chromatography matrix immediately after the first fraction.

Including both leading and trailing fractions increases the overall purification yield of the process, and can also allow the equipment used in the process of the invention to be simplified. For example, the number of storage containers used to hold the second fractions can be reduced, thus reducing the number of feed lines and necessary valve positions needed. A further advantage is that the leading fraction and the trailing fraction can be loaded homogeneously to the chromatography matrix, which is beneficial as e.g. it allows the processing parameters such as elution time etc to be easily predicted.

Preferably, therefore, in the processes of the invention the second fraction comprises or consists of the leading fraction immediately preceding the first fraction and/or the trailing fraction immediately following the first fraction. Preferably, the leading fraction and trailing fraction are re-loaded to the chromatography matrix separately or are combined and re-loaded to the same chromatography matrix.

In a similar manner, with particular reference to the second aspect discussed above, preferably:
  i) the one or more fractions of the eluate re-loaded to the same chromatography matrix are different from one or more fractions of the eluate having a desired characteristic;
  ii) one or more fractions of the eluate re-loaded to the chromatography matrix elute from the chromatography matrix prior to the one or more fractions of the eluate having a desired characteristic; and/or one or more fractions of the eluate re-loaded to the chromatography matrix elute from the chromatography matrix after the one or more fractions of the eluate having a desired characteristic; and optionally
  iii) the one or more fractions of the eluate re-loaded to the chromatography matrix which elute from the chromatography matrix prior to the one or more fractions of the eluate having a desired characteristic; and the one or more fractions of the eluate re-loaded to the chromatography matrix which elute from the chromatography matrix after the one or more fractions of the eluate having a desired characteristic are:
    i) re-loaded to the same chromatography matrix separately; or
    ii) are combined and re-loaded to the same chromatography matrix.

Multiple Fractions

As described above, the processes of the invention involve loading feed onto a chromatography matrix and eluting the target biomolecule (the compound of interest) from the matrix. In addition to first fractions comprising purified product biomolecule (and thus having a desired characteristic as defined herein), the eulate also comprises second fractions comprising at least one impurity (and thus having an undesired characteristic as defined herein). The processes of the invention can give rise to one or multiple of such second fractions. As described in more detail below, multiple second fractions can arise in various ways, including by collecting multiple second fractions from a single cycle of the processes of the invention, or by performing multiple cycles of the processes of the invention and collecting either single or multiple second fractions in each cycle.

Preferably, in the processes of the invention, more than one second fraction may be collected. In such circumstances, the multiple second fractions collected may either be individually (re)-loaded to the chromatography matrix; or may be combined ("pooled together") and reloaded to the chromatography matrix as a combined fraction. In other words, if the one or more of the fractions of the eluate are two or more fractions of the eluate, the two or more fractions of the eluate are individually re-loaded to the same chromatography matrix. Alternatively, the two or more fractions of the eluate may be combined and re-loaded to the same chromatography matrix as a combined fraction.

The process of the invention can give rise to multiple second fractions in a variety of ways. For example, the feedstock comprising the product biomolecule (i.e. the mixture comprising the compound of interest) may be loaded to the chromatography matrix in multiple portions, each portion giving rise to a first fraction and a second fraction. In such circumstances the second fractions collected may be individually (re)-loaded to the chromatography matrix. Alternatively, the second fractions may be pooled together; and the pooled second fractions loaded to the chromatography matrix such that the product biomolecule in the second fraction binds to the chromatography matrix.

Another example is when a second fraction comprising a leading fraction is collected separately to a second fraction comprising a trailing fraction. The second fraction comprising the leading fraction and the second fraction comprising the trailing fraction may thus be individually (re)-loaded to the chromatography matrix. Alternatively, the second fractions may be pooled together; and the pooled second fractions loaded to the chromatography matrix such that the product biomolecule in the pooled second fractions binds to the chromatography matrix.

Holding Stage

In the processes of the invention, once the feed from the feedstock has been loaded onto the chromatography column and the first and second fractions eluted, the second fraction(s) are held in one or more container(s) prior to being re-loaded to the chromatography matrix. This holding stage corresponds to step (c) in the claimed process.

The hold time can be controlled according to the process at issue. Preferably, the hold time is at least 5 minutes, more preferably at least 30 minutes, e.g. at least 1 hour, for example at least 2 hours. Longer hold times are also suitable, such as hold times of at least 5 hours, 10 hours, 24 hours, one day, two days, 7 days, 14 days, one month, 2 months, 6 months or a year.

Accordingly, in the invention, step (c) preferably comprises holding the second fraction(s) for at least 5 minutes. Step (c) may preferably comprise holding the second fraction(s) overnight.

An advantage of the holding step in the processes of the invention is that modifications can be made to the chromatography equipment or the fractions if required. For example, as described further below, the fractions eluted from the chromatography matrix can be further processed prior to being re-loaded onto the column. Alternatively, the chromatography matrix can be exchanged, cleaned or renewed during the hold time. A prolonged hold time can also be advantageous in terms of improving convenience for the operator. For example, hold times can be scheduled to run overnight, or across weekends, and can thus avoid the need for operators to work antisocial hours. Another advantage of the holding step is that the fraction(s) eluted from the chromatography matrix (in particular the second fraction(s)) can be tested as described herein during the holding step.

Processing

In the processes of the invention, the second fraction(s) that are re-loaded to the chromatography matrix may be processed in order to promote binding of the biomolecule by the chromatography matrix. The second fraction(s) are preferably processed prior to or during re-loading to the chromatography matrix in order to promote binding of the biomolecule by the chromatography matrix. However, the second fraction(s) may be processed during their elution from the chromatography matrix. Accordingly, in the claimed process of the invention, processing preferably takes place during step (b) and/or step (c) and/or step (d) of the process, preferably during step (c) and/or step (d); most preferably during step (c) of the process.

In the processes of the invention, processing the second fraction(s) preferably comprises altering the pH, ionic strength, concentration, temperature and/or solvent of the second fraction(s) (i.e., with reference to the second aspect of the process above, the one or more of the fractions of the eluate which are processed prior to or during re-loading). Processing may also comprise mixing and/or degassing. Processing may also comprise stirring or agitation. Suitable techniques are for processing samples as described herein are known in the art. For example, altering the pH of a sample may comprise addition of acid or base. Altering ionic strength may be achieved by addition or sequestration of ionic substances such as salts, or by dilution (e.g. in water or buffer). Altering concentration may be achieved by concentrating the sample (e.g. using a vacuum filter assembly) or by dilution (e.g. in water or buffer). Altering the temperature may be achieved by heating or cooling using conventional equipment. Altering the solvent of a sample may be achieved by buffer or solvent exchange e.g. by diafiltration.

The processes of the invention may beneficially involve testing the second fraction(s). Preferably such testing is non-destructive testing, preferably in-line testing as described herein. As described in more detail below, testing the second fraction(s) preferably comprises determining one or more of the concentration of the product biomolecule; the concentration of impurities; the identity of impurities; the pH; the ionic strength; the temperature; the solvent; and/or the gas concentration of the second fraction(s).

In order to effectively process the fractions of the eluate (i.e. the second fraction(s)), it is typically necessary to first determine the characteristics of such fractions which have an impact on the binding of the compound of interest to the chromatography matrix. For example, prior to altering the pH of a sample, it is typically necessary to determine the pH of the sample. Similarly, prior to altering the ionic strength, concentration and/or temperature of a sample, it is typically necessary to determine the ionic strength, concentration and/or temperature of the sample, respectively. Methods for determining said characteristics are known to the person skilled in the art.

The steps of determining said characteristics and of processing the fractions may be immediately linked to each other, i.e. the characteristics are determined and immediately after determination one or more of said characteristics are changed such that the compound of interest contained in the processed fraction may bind to the chromatography matrix upon application. Alternatively, the steps of determining said characteristics and of processing may be separated from each other. Such separation may be a separation in time, i.e. there is a time gap between determining said characteristics and processing the one or more fractions of the eluate, i.e. the characteristic is determined and only after lapse of a certain period of time one or more of said characteristics are changed such that the compound of interest contained in the processed fraction may bind to the chromatography matrix upon application. Typically, such time gap is at least 30 minutes, 1 hour, 2 hours, 5 hours, 10 hours, 24 hours, one day, two days, 7 days, 14 days, one month, 2 months, 6 months or a year. Short time gaps such as time gaps not exceeding 2 days, more preferably not exceeding 24 hours e.g. not exceeding 10 hours, for example not exceeding 5 hours e.g. not exceeding 2 hours more preferably not exceeding 1 hour e.g. not exceeding 30 minutes can be beneficial as potential for degradation and/or contamination of the compound of interest (i.e. the product biomolecule) can be minimized. Longer time gaps such as time gaps exceeding 2 days, such as those of at least 7 days, such as at least 14 days, one month, 2 months, 6 months or a year or longer can be beneficial if multiple batches of protein have to be purified; typically in such cases the fractions of the eluate (i.e. the second fractions) are frozen over the delay to minimize potential for degradation and/or contamination.

The characteristics of the one or more of the fractions of the eluate (i.e. the second fraction) may be determined on-line, at-line or offline. Determining said characteristics online preferably means that said characteristics are determined in the process according to the invention, e.g. with a detector connected to the outlet of the chromatography matrix or positioned at or in the container(s) in which said one or more fractions of the eluate is/are collected in real time. Determining said characteristics at-line preferably means that said characteristics are determined with samples taken from the outlet of the chromatography matrix or the container(s) in which said one or more fractions of the eluate is/are collected. Determining said characteristics offline preferably means that said characteristics are determined with samples taken from the outlet of the chromatography matrix or the container(s) in which said one or more fractions of the eluate is/are collected and measured after a delay on a detector placed distant, i.e. in a separate room from the matrix. Preferably, the characteristics of the fractions are determined on-line or at-line, more preferably on-line.

Additional Feedstock

In the invention, the second fraction is re-loaded to the chromatography matrix with additional feed from the feedstock (i.e. with additional mixture comprising the compound of interest). The additional feed is loaded simultaneously with or sequentially to the second fraction. Additional feed can be added to the second fraction(s) held in the container(s) before the resulting mixture is loaded to the chromatography matrix. Alternatively, additional feed can be loaded to the chromatography matrix before, during or after loading of the second fraction(s) from the container(s).

Accordingly, step (d) comprises loading additional feed from the feedstock to the chromatography matrix simultaneously with or sequentially to the second fraction. In other words, with particular reference to the second aspect discussed above, the one or more of the fractions of the eluate are re-loaded to the same chromatography matrix together with the mixture comprising compound of interest, or at least with a part of said mixture. The mixture comprising the compound of interest which is loaded to the chromatography matrix together with the fractions of the eluate has preferably not undergone any operational chromatography cycle of the process of the present invention. It is, however, within the invention that such mixture has already undergone any form of down-stream processing.

In the invention, step (d) comprises loading additional feed from the feedstock to the chromatography matrix simultaneously with or sequentially to the second fraction. The second fraction is preferably processed prior to or during re-loading with the feed. In other words, with particular reference to the second aspect discussed above, in the invention, the fractions of the eluate are re-loaded to the chromatography matrix together with all or part of the mixture comprising compound of interest, and preferably the one or more fractions of the eluate combined with the mixture comprising the compound of interest are processed prior to or during re-loading such that the compound of interest contained in the one or more fractions of the eluate combined with the mixture comprising the compound of interest binds to the chromatograph matrix upon re-loading.

The combination of the second fraction(s) with additional feed from the feedstock (i.e. the combination of one or more fractions of the eluate with the mixture comprising the compound of interest) is also referred to herein as the combined load. As to such processing of the combined load, the same applies as outlined herein in connection with the processing of the one or more of the fractions of the eluate, described above.

Loading Feed

As will be apparent from the above description of the invention, the processes of the invention involve loading feed from a feedstock (i.e. a mixture comprising the product biomolecule, i.e. the compound of interest) to a chromatography matrix such that the product biomolecule binds to the chromatography matrix.

The invention does not require that the entire feedstock is loaded to the chromatography matrix in one volume, although this is not excluded. The invention may thus involve loading the entirety of the feedstock to the chromatography matrix in one volume. More preferably, however, a part of the total volume of the feedstock (i.e., feed from the feedstock) is loaded to the chromatography matrix and the process of the invention performed. Additional feed may then be loaded onto the chromatography matrix in accordance with the invention as described herein. For example, as explained above, step (d) of the process involves loading additional feed from the feedstock to the chromatography matrix simultaneously with or sequentially to the second fraction.

In other words, with particular reference to the second aspect discussed above, a first volume of the mixture comprising the compound of interest is preferably loaded in the first operational chromatography cycle from the first container to the chromatography matrix operated such that the compound of interest binds to the chromatography matrix. Accordingly, in such embodiment not the entire mixture comprising the compound of interest which is to be subjected to the process of the invention is in a first operational chromatography cycle loaded to the chromatography matrix.

Preferably, in the invention, the feedstock is loaded onto the chromatography matrix until a desired loading is reached. For example, the feedstock may preferably be loaded onto the chromatography matrix until between 40 and 100%, such as from 50% or 60% to 90% such as from 70% to 80% of the static binding capacity of the chromatography matrix is reached. In other words, when loading the mixture comprising the compound of interest from the first container to the chromatography matrix operated such that the compound of interest binds to the chromatography matrix, the loading is typically such that the compound of interest binds to the chromatography matrix until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached. Loading feedstock to the chromatography matrix to a load below 100% of the static binding capacity of the matrix can sometimes be advantageous, for example in applications where increased separation of the target biomolecule and impurities is desired.

Flow-Through

As those skilled in the art will appreciate, when loading feedstock comprising the product biomolecule onto the chromatography matrix, either all or only part of the total amount of product biomolecule in the feed may bind to the chromatography matrix. Excess product biomolecule (compound of interest) which does not bind to the chromatography matrix remains uncaptured by the matrix, and may be collected from the chromatography matrix as flow-through. This can occur when excess feed is loaded to the chromatography matrix such that the static binding capacity of the matrix is exceeded.

Flow-through if present may in some circumstances comprise high levels of the product biomolecule (the compound of interest) and may therefore be valuably recovered for purification. Flow-through may arise if excess feed from the feedstock is added to the chromatography matrix such that the static binding capacity of the matrix is exceeded, e.g. if the static binding capacity of the matrix is exceeded by at least 10% such as at least 20%, e.g. at least 50% for example the static binding capacity of the matrix may be exceeded by at least 100% or more. Excess load can be deliberately applied in the methods of the invention e.g. to maximize purification speed. Thus, step (a) of the claimed process may comprise loading feed from the feedstock onto the chromatography matrix such that the dynamic binding capacity of the chromatography matrix is exceeded, and collecting flow-through containing unbound product biomolecule. The flow-through thus collected may be re-loaded onto the chromatography matrix, e.g. in a further cycle of the process or together with the second fraction of the eluate and/or the additional feed from the feedstock in step (d) of the process.

The high potential value of flow-through means that its recovery and purification to obtain the compound of interest (the product biomolecule) is desirable.

Accordingly, step (a) of the claimed process of the invention preferably further comprises collecting flow-through containing unbound product biomolecule that does not bind to the chromatography matrix; and step (d) preferably further comprises loading the flow-through to the chromatography matrix simultaneously with or sequentially to the second fraction(s) and/or the additional feed. Step (d) may comprise loading all or only part of the flow-through. When only part of the flow-through is loaded in step (d), the remainder of the flow-through is preferably retained and is subsequently loaded onto the chromatography matrix e.g. together with additional feed from the feedstock. The flow-through is preferably held in one or more container(s) for a hold time as discussed below. The container(s) may be the same container(s) that are used to hold the second fraction(s). Alternatively the container(s) used to hold the flow-through may be separate to the container(s) used to hold the second fraction(s). The flow-through may preferably be processed to promote binding of the product biomolecule to the chromatography matrix. Any suitable processing step, such as any of the processing steps described above for the second fraction(s) can be used.

Although the flow-through may be loaded to the chromatography matrix simultaneously with or sequentially to the second fraction(s), the flow-through may alternatively be re-loaded to the chromatography matrix separately to the second fraction(s). For example, the flow-through can be loaded to the chromatography matrix simultaneously with or sequentially to additional feed from the feedstock (i.e. in step (a) of the process).

When flow-through is reloaded to the chromatography matrix, whether in step (d) or step (a) of the process, the chromatography matrix is preferably loaded until between 40 and 100%, such as from 50% or 60% to 90% such as from 70% to 80% of the static binding capacity of the chromatography matrix is reached. This reduces the likelihood of product biomolecule repeatedly flowing through the chromatography matrix without being bound by the matrix.

Accordingly, with particular reference to the process of the second aspect discussed above, such process preferably involves, prior to eluting the compound of interest from the chromatography matrix and collecting the eluate containing the compound of interest as fractions of the eluate, the steps of ab) collecting flow-through containing unbound compound of interest in a second container, and ac) in a further operational chromatography cycle re-loading the flow-through from the second container to the same chromatography matrix operated such that the compound of interest binds to the chromatography matrix.

Such process may also preferably comprise, prior to eluting the compound of interest from the chromatography matrix and collecting the eluate containing the compound of interest as fractions of the eluate, the steps of ab) collecting flow-through containing unbound compound of interest in a second container, and ac) re-loading the flow-through from the second container to the same chromatography matrix and additionally loading fresh load mixture in a further operational chromatography cycle operated such that the protein of interest binds to the chromatography matrix.

The fresh load mixture may be a second volume of feed from the feedstock. Accordingly, the method preferably comprises the step of re-loading the flow-through from the second container and loading a second volume of the compound of interest from the first container to the same chromatography matrix in the further operational chromatography cycle operated such that the protein of interest binds to the chromatography matrix. It is within the present invention that such second volume of the compound of interest is a second volume of the mixture comprising the compound of interest.

Preferably, in the step of reloading the flow-through from the second container the chromatography matrix is operated such until 40 to 100%, 50 to 100%, 60 to 100%, 70 to 100%, 80 to 100%, 90 to 100%, 70 to 90% or 70 to 80%, 60 to 90%, 60 to 80% of the static binding capacity of the chromatography matrix is reached. Preferably between 40 and 100%, such as from 50% or 60% to 90% such as from 70% to 80% of the static binding capacity of the chromatography matrix may be reached.

Preferably, with particular reference to the process of the second aspect discussed above, the flow-through collected in the second container and the one or more of the fractions of the eluate are separately re-loaded in an operational chromatography cycle. It is within the present invention that only a part of the flow-through, i.e. a part of the volume of the flow-through and/or only a part of the one or more of the fractions of the eluate, i.e. only a part of the volume of the one or more of the fractions of the eluate, are separately re-loaded in an operational chromatography cycle. Preferably, the flow-through collected in the second container and the one or more of the fractions are separately re-loaded in the same operational chromatography cycle, preferably the chromatography cycle immediately following the first operational chromatography cycle.

Alternatively, the flow-through collected in the second container and the one or more of the fractions may preferably be separately re-loaded in different operational chromatography cycles. It is within the present invention that the one or more of the fractions of the eluate is/are re-loaded to the same chromatography matrix prior to the flow-through collected in the second container. It is, however, also within the present invention that the flow-through collected in the second container is re-loaded to the same chromatography matrix prior to the one or more fractions of the eluate.

In an alternative embodiment, the flow-through and the one or more of the fractions of the eluate may be combined and re-loaded as a combination to the same chromatography matrix operated such that the compound of interest binds to the chromatography matrix. It is within the present invention that said combination is processed as disclosed herein in connection with the processing of the one or more of the fractions of the eluate.

Accordingly, in the second aspect of the invention, a first volume of the mixture comprising the compound of interest may preferably be loaded in the first operational chromatography cycle from the first container to the chromatography matrix operated such that the dynamic binding capacity of the chromatography matrix is exceeded, and the process comprise, prior to eluting the compound of interest from the chromatography matrix and collecting the eluate containing the compound of interest as fractions of the eluate, the steps of ab) collecting flow-through containing unbound compound of interest in a second container; and ac) in a further operational chromatography cycle re-loading the flow-through from the second container and loading a second volume of the compound of interest from the first container to the same chromatography matrix, operated such that the dynamic binding capacity of the chromatography matrix is exceeded. It is within the present invention that such second volume of the compound of interest is a second volume of the mixture comprising the compound of interest.

Preferably, in the step of loading a first volume of the mixture comprising the compound of interest in the first operational chromatography cycle from the first container to the chromatography matrix operated such that the dynamic binding capacity of the chromatography matrix is exceeded, the loading of the protein of interest is stopped when at least 40% 50%, 60%, 70%, 80%, 90% or 100% of the maximum static binding capacity is reached.

Preferably, in the processes of the invention, the collection of the flow-through is started at a predetermined first concentration of product biomolecule (protein of interest) in the flow-through and stopped at a predetermined second concentration of product biomolecule (protein of interest) in the flow-through. The collection of product biomolecule (protein of interest) in the flow-through is preferably started at a concentration of 0.05 mg/ml, 0.1 mg/ml or 0.2 mg/ml of protein of interest in the flow-through and/or stopped at a concentration of 0.6 mg/ml, 1 mg/ml, 2 mg/ml, 3 mg/ml, 4 mg/ml or 5 mg/ml of protein of interest in the flow-through. Preferably, a predetermined fraction of the flow-through, such as for example 50%, 40%, 30%, 20%, 10% or 5% of the flow-through, is collected in the second container.

Preferably, in one embodiment, the flow-through collected (e.g. in the second container) is not processed prior to or while being re-loaded onto the chromatography matrix, e.g. in a further operational chromatography cycle. Preferably, the flow-through collected (e.g. in the second container) is, following the completion of the chromatography cycle, directly re-loaded onto the chromatography matrix in the next operational chromatography cycle. Preferably, in another embodiment, the flow-through collected (e.g. in the second container) is processed prior to or while being re-loaded onto the chromatography matrix e.g. in a further operational chromatography cycle. Processing may be, for example stirring or agitation, dilution (e.g. in water or buffer), concentration adjustment, (e.g. using a vacuum filter assembly), pH adjustment, conductivity adjustment, buffer or solvent exchange, cooling or heating or any combination thereof. Processing may be as described above for the second fraction.

Preferably, the flow-through from multiple separate operational chromatography cycles (i.e. several cycles of a process of the invention) collected (e.g. in the second container) is pooled and re-loaded onto the same chromatography matrix in another cycle. The flow-through from two, three, four, five, six, seven, eight, nine, ten or more than ten operational chromatography cycle may be collected (e.g. in a single second container or in a second, third, fourth or further containers) and reloaded onto the chromatography matrix, e.g. in a further operational chromatography cycle.

Preferably, in one embodiment of the processes of the invention, the collected flow-through is re-loaded (e.g. from the second container) onto the chromatography matrix in a subsequent operational chromatography cycle before a new batch of the mixture from the first container containing the protein interest is loaded onto said chromatography matrix. Re-loading the flow-through in a subsequent chromatography cycle before the mixture from the first container containing the compound of interest, preferably the protein interest, allows complete binding of the recycled compound of interest, preferably the protein of interest, by the empty column which ensures it is captured in only two cycles. Alternatively, in another embodiment, the collected flow-through is preferably re-loaded from the second container onto the chromatography matrix in a subsequent operational chromatography cycle after or together with a new batch of the mixture from the first container containing the compound of interest, preferably the protein interest, is loaded onto said chromatography matrix. In other words, flow-through may be loaded to the chromatography matrix either separately from additional feed from the feedstock, or together with additional feed from the feedstock.

Preferably, flow-through collected in the second container is stored for at least 30 minutes, 1 hour, 2 hours, 5 hours, 10 hours, 24 hours, one day, two days, 7 days, 14 days, one month, 2 months, 6 month or a year. Short storage periods (hold times) such as hold times not exceeding 2 days, more preferably not exceeding 24 hours e.g. not exceeding 10 hours, for example not exceeding 5 hours e.g. not exceeding 2 hours more preferably not exceeding 1 hour e.g. not exceeding 30 minutes can be beneficial as potential for degradation and/or contamination of the product biomolecule (i.e. the compound of interest) in the flow-through can be minimized. Longer hold times such as hold times exceeding 2 days, such as those of at least 7 days, such as at least 14 days, one month, 2 months, 6 months or a year or longer can be beneficial if multiple batches of flow-through have to be purified; typically in such cases the flow-through is frozen over the hold time to minimize potential for degradation and/or contamination.

Feedstock

As described herein, the mixture comprising the product biomolecule (i.e. the compound of interest) is also known as the feedstock. In the processes of the invention, feed from the feedstock is loaded onto the chromatography matrix.

Preferably, in one embodiment, the feedstock (mixture) comprises the product biomolecule (i.e. the compound of interest, preferably a protein of interest); and prokaryotic, e.g. bacterial, host cell contaminants, such host cell protein, nucleic acid or lipid. Preferably, in another embodiment, the feedstock (mixture) comprises the product biomolecule (compound of interest, preferably a protein of interest), and eukaryotic, e.g. mammalian, host cell contaminants, such host cell protein, nucleic acid or lipid.

Preferably, in the invention, the feedstock (i.e. the mixture comprising the compound of interest) has a volume of at least 20 litres, e.g. at least 50 litres, such as at least 60 L, e.g. at least 80 L, more preferably at least 100 litres for example at least 500 litres e.g. at least 1000 L or more, e.g. at least 5000 L, such as at least 10000 L e.g. up to at least 50,000 L, 100,000 L or more. The mixture/feedstock may thus preferably have a volume of more than 1,000 L, e.g. between 1000 L and 50,000 L or 100,000 L, preferably between 5,000 L and 20,000 L, e.g. about 10,000 L. Smaller volumes of between 2 L and 100 L e.g. between 20 L and 50 L may also be used.

Preferably, the product biomolecule (i.e. the compound of interest) is selected from the group comprising a protein, an antibody, an antibody fragment, a nucleic acid molecule (i.e. a polynucleotide), a polypeptide and a small molecule, for example the compound of interest (i.e. the product biomolecule) is preferably selected from the group comprising a protein, an antibody, an antibody fragment, a polynucleotide and a polypeptide. Preferably, the product biomolecule (i.e. the compound of interest) is selected from the group comprising a protein, an antibody, an antibody fragment, a nucleic acid molecule and a small molecule. Preferably, the product biomolecule (i.e. the compound of interest) is a protein. Preferably, the product biomolecule (i.e. the compound of interest) is an antibody or an antibody fragment.

Chromatography Matrices

Many chromatography techniques are known in the art and are compatible with the methods of the invention.

Almost all current industrial antibody purification platforms use Protein A. Protein A is a cell surface protein found in the cell wall of the bacteria *Staphylococcus aureus* that binds to the Fc portion of mammalian immunoglobulin. Protein A has a high affinity to human $IgG_1$ and $IgG_2$ and a moderate affinity to human IgM, IgA and IgE antibodies.

Consequently, protein A purification is not well suited for antibody fragments that lack the Fc portion. However, protein A chromatography is well suited to some antibodies (especially those having an Fc portion) and is compatible with the methods of the invention. Affinity chromatography separates proteins on the basis of a reversible interaction between a protein (or group of proteins) of interest and a specific ligand coupled to a chromatography matrix. The interaction between the protein of interest and ligand coupled to the chromatography matrix can be a result of electrostatic or hydrophobic interactions, van der Waals' forces and/or hydrogen bonding. To elute the target molecule from the affinity medium the interaction can be reversed, either specifically using a competitive ligand, or non-specifically, by changing the pH, ionic strength or polarity. Affinity purification requires a ligand that can be covalently attached to a chromatography matrix. The coupled ligand must retain its specific binding affinity for the target molecules and, after washing away unbound material, the binding between the ligand and target molecule must be reversible to allow the target molecules to be removed in an active form. Despite its common use, affinity chromatography is costly, particularly at the industrial scale necessary to purify therapeutic proteins. The methods of the invention are compatible with affinity chromatography and as they are intended to maximize process efficiency they address at least in part the high costs involved.

Ion exchange chromatography can be used to purify ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. Elution of molecules that are bound to the solid phase is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). Two general types of interaction are known: Anionic exchange chromatography mediated by negatively charged amino acid side chains (e.g. aspartic acid and glutamic acid) interacting with positively charged surfaces and cationic exchange chromatography mediated by positively charged amino acid residues (e.g. lysine and arginine) interacting with negatively charged surfaces. Anion exchangers can be classified as either weak or strong. The charge group on a weak anion exchanger is a weak base, which becomes de-protonated and, therefore, loses its charge at high pH. Diethylaminoethyl (DEAE)-cellulose is an example of a weak anion exchanger, where the amino group can be positively charged below pH-9 and gradually loses its charge at higher pH values. DEAE or diethyl-(2-hydroxy-propyl)aminoethyl (QAE) have chloride as counter ion, for instance.

An alternative to elution by increase in ion strength of the elution buffer (elution chromatography) is elution using molecules which have a higher dynamic affinity for the stationary phase than the bound protein. This mode of performing ion-exchange chromatography is called displacement chromatography. Displacement chromatography is fundamentally different from any other modes of chromatography in that the solutes are not desorbed in the mobile phase modifier and separated by differences in migration rates. In displacement, molecules are forced to migrate down the chromatographic column by an advancing shock wave of a displacer molecule that has a higher affinity for the stationary phase than any component from the feed stream. It is this forced migration that results in higher product concentrations and purities compared to other modes of operation. of high retention, followed by a constant infusion of a displacer solution into the column.

These and other chromatography techniques known in the art are compatible with the methods of the invention. As will be apparent from the above discussion, the processes of the invention requires loading of the product biomolecule (the protein of interest) to a chromatography matrix such that the product biomolecule binds to the chromatography matrix. This kind of chromatography mode is known as bind-and-elute mode. This chromatography is different from a flow-through mode such as that described in WO 2014/158231.

Preferably, the process comprises more than one chromatography step, and two, three, four or all chromatography steps may be operated such that the flow-through containing unbound protein of interest is collected (e.g. in a container other than the container from which the chromatography matrix has been loaded), and the flow-through is re-loaded (e.g. from such container) to the same chromatography matrix in a later operational chromatography cycle. Preferably, the process comprises one, two, three, four or more than four chromatography steps. Preferably, one, two, three, four or all chromatography steps are performed on a chromatography column. Preferably, the process comprises three chromatography steps, wherein the three chromatography steps are Protein A chromatography followed by cation exchange chromatography followed by anion exchange chromatography. In one embodiment of the process of the invention the eluate of the Protein A chromatography is subjected to cation exchange chromatography operated in in bind and elute mode from where an eluate containing the protein of interest is recovered, and such eluate is subjected to anion exchange chromatography to produce a flow-through containing the protein of interest. It is understood by the skilled artisan that the process according to the invention may comprise other steps between each of the three chromatography steps, such as for example diafiltration.

Preferably, the chromatography is selected from affinity chromatography, such as Protein A chromatography, anion or cation exchange chromatography, hydrophobic interaction chromatography, mixed-mode chromatography, such as hydroxyapatite chromatography, chiral chromatography or dielectric chromatography. Accordingly, preferably the chromatography matrix is selected from:
   an ion exchange chromatography matrix;
   a hydrophobic interaction chromatography matrix;
   an affinity chromatography matrix;
   a mixed-mode chromatography matrix;
   a chiral chromatography matrix; and
   a dielectric chromatography matrix.

Preferably, the chromatography matrix/matrices for one, two, three, four or all chromatography steps is/are a chromatography column(s). In other words, preferably in the processes of the invention, the chromatography matrix is in a chromatography column.

Preferably, the chromatography matrix has a bed volume of at least 1 litre, e.g. at least 4 litres, such as at least 5 litres, more preferably at least 10 L, e.g. at least 20 L for example at least 30 L, preferably more than 50 L, typically more than 75 L, more preferably at least 100 L or at least 200 L, for example preferably between 20 L and 200 L, e.g. between 30 L and 100 L for example between 50 L and 100 L. In other words, preferably, at least one of the chromatography matrix is a chromatography column having a bed volume of more than 1 L, more than 20 L, more than 30 L, more than 50 L, more than 75 L, more than 100 L or more than 200 L, preferably between 20 L and 200 L, 30 L and 100 L or 50 L and 100 L.

Preferably, in the methods of the invention, in step (b) the volume of the eluate is at least equal to the bed volume of the chromatography matrix. More preferably, the volume of the eluate is at least 2 times the bed volume of the chromatography matrix, for example at least 5 times the bed volume of the chromatography matrix, for example at least 10 times the bed volume of the chromatography matrix, such as at least 15 times the bed volume of the chromatography matrix, for example at least 20 times the bed volume of the chromatography matrix or more. Preferably the volume of the eluate is between 2 times and 20 times the bed volume of the chromatography matrix.

In other embodiments, preferably the chromatography matrix is a chromatography membrane or a monolith adsorber.

Preferably, one, two, three, four or all chromatography steps is/are operated on a membrane or monolith adsorber.

Preferably, one, two, three, four or all chromatography steps is/are operated on a single chromatography column, membrane adsorber or monolith adsorber.

In the invention, higher flow rates can be used than are typically employed in conventional chromatography techniques. In part this can be achieved as any decreasing separation between the target biomolecule (the compound of interest) and impurities in the feedstock (the mixture comprising the compound of interest) is compensated for by reloading the second fractions onto the chromatography matrix for further purification. Accordingly, the processes of the invention may preferably involve eluting the product biomolecule (the compound of interest) from the chromatography matrix at a flow rate of at least 0.05 to 0.5 chromatography matrix volumes per minute, such as at least about 0.1 to about 0.4 chromatography matrix volumes per minute, e.g. at least about 0.2 to about 0.3 chromatography matrix volumes per minute.

The processes of the invention may preferably involve eluting the product biomolecule (the compound of interest) from the chromatography matrix at a flow rate of from about 60 to about 900 cm/h (wherein the cm notation refers to the bed height of the chromatography matrix; typically about 20 cm to about 30 cm, preferably about 20 cm; and wherein h=hour), such as from about 120 to about 720 cm/h, e.g. from about 240 to about 540 cm/h e.g. from about 300 to about 450 cm/hour.

As will be apparent from the above discussion, an advantage of the processes of the invention is that the process length is not limited to the volume of the chromatography matrix. In other words, the collection of the second fractions before their reloading allows volumes of feedstock in excess of the volume of the chromatography matrix to be processed in accordance with the methods of the invention. Accordingly, in the processes of the invention, the process length is preferably greater than the volume of the chromatography matrix. This is beneficially achieved by the use of a container to store the second fraction(s) (i.e. those fractions of the eluate which are re-loaded to the chromatography matrix).

Any suitable container can be used, e.g. to store the second fraction(s) and/or flow-through. Those skilled in the art will recognize that the second container can be in line with the chromatography equipment or can be an external container. Appropriate valves etc will allow the fractions to be directed to the container as required.

Additional Process Steps

Preferably, the first fractions from multiple cycles of the processes of the invention may be combined or pooled together. Accordingly, the process of the invention preferably comprises combining each of the first fractions.

The processes of the invention may preferably comprise diafiltering and/or concentrating the first fractions (the fractions of the eluate comprising the target biomolecule, i.e. the compound of interest). The first fractions are preferably concentrated after optional diafiltration to a final desired concentration appropriate for therapeutic use.

The processes of the invention may preferably comprise nanofiltering the purified product biomolecule. Nanofiltration may be conducted using any suitable apparatus. Typically, nanofiltration is conducted using a polymer (e.g. polyethylene terephthalate) or metal (e.g. aluminium) membrane having a pore size of from about 1 nm to about 10 nm.

The processes of the invention may preferably further comprise subjecting the purified product biomolecule to further chromatographic purification. Any suitable chromatographic purification can be used such as any of the chromatography processes discussed herein.

The processes of the invention may preferably comprise chemically modifying the purified product biomolecule. Any suitable chemical modification can be made. For example, the product biomolecule can be modified by reduction and/or pegylation. The product biomolecule can be modified by attaching it to one or more entities selected from radionuclides, drugs, toxins, polymers (e.g. PEG), metal chelates, fluorophores, haptens, and the like. Attachment may be achieved by any suitable means, such as EDC/NHS coupling or via disulphide formation between reactive thiol groups of proteins. Reduction can be achieved using chemical reductants.

The processes of the invention may preferably further comprise formulating the target biomolecule/the compound of interest with a pharmaceutically acceptable excipient, diluent or adjuvant.

Accordingly, the invention also provides a method of manufacture of a protein of interest, said method comprising the process of the invention, including any embodiment thereof, wherein the compound of interest of target biomolecule is a protein. The invention also provides a protein, such as an antibody or an antibody fragment, obtainable by such a method.

The invention also provides a compound of interest or a target biomolecule obtainable by the process of the invention as disclosed herein.

Definitions

The term "anion exchange chromatography" as used herein refers to a chromatography wherein the solid phase is positively charged, e.g. having one or more positively charged ligands, such as quaternary amino groups, attached thereto. Commercially available anion exchange matrices include DEAE cellulose, QAE SEPHADEX™, FAST Q SEPHAROSE™ Capto Q and Capto Q Impres (GE Healthcare), Unosphere and Nuvia Q (BioRad), GigaCap Q (Tosoh), Mustang Q XT (Pall), Fractogel Q and Eshmuno Q (Merck Millipore) and anion exchange membrane adsorbers such as SartoBind Q (Sartorius), and monolith adsorbers such as QA monoliths (Bia Separations.

The term "antibody" or "antibodies" as used herein, refers to monoclonal or polyclonal tetrameric full length antibodies comprising two heavy and two lights chains. The two heavy chains and the two light chains may be identical or different, e.g. in bispecific antibodies such as Biclonics® or the DuoBody®. The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine. Preferred molecular targets for antibodies encompassed by the present invention include CD polypeptides such as CD3, CD4, CD8, CD19, CD20, CD22, CD34, CD38, CD40 and CD40-L; FcRN; OX40; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either α or β subunits thereof (e.g. anti-CD11a, anti-CD18 or anti-CD11b antibodies); chemokines and cytokines or their receptors such as IL-1 α and β, IL-2, IL-6, the IL-6 receptor, IL-12, IL-13, IL-17A and/or IL-17F, IL-18, IL-21, IL-23, TNFα and TNFβ; growth factors such as VEGF; IgE; blood group antigens; flk2/flt3 receptor; obesity (OB) receptor; mpl receptor; CTLA-4; polypeptide C; PD1, PD-L1, PCSK9; sclerostin; etc.

The term "antibody fragment" or "antibody fragments" as used herein, refers a portion of an antibody, generally the antigen binding or variable region thereof. Examples of antibody fragments include any antibody that lacks the or has no Fc portion. Examples of antibody fragments include also such as Fab, Fab', F(ab')$_2$, and Fv and scFv fragments; as well as diabodies, including formats such as BiTEs® (Bi-specific T-cell Engagers) and DARTs™ (Dual Affinity Re-Targeting technology), triabodies, tetrabodies, minibodies, domain antibodies (dAbs), such as sdAbs, VHH and VNAR fragments, single-chain antibodies, bispecific, trispecific, tetraspecific or multispecific antibodies formed from antibody fragments or antibodies, including but not limited to Fab-Fv, Fab-scFv, Fab(Fv)$_2$ or Fab-(scFv)$_2$ constructs. Antibody fragments and derivatives as defined above are known in the art (Kontermann 2012). For the purpose of clarity Fab-Fv should be understood to refer to a construct containing one Fv region and one Fab region joined in any order, i.e. Fab-Fv, or Fv-Fab, wherein the last amino acids in one region are followed by the first amino acids in the next region or vice versa. Similarly Fab-scFv should be understood to refer to a construct containing one scFv region and one Fab region joined in any order and in the case of the Fab to either polypeptide chain, i.e. Fab-scFv, or scFv-Fab, wherein the last amino acid in one region is followed by the first amino acid in the next region or vice versa. In the same manner Fab-(Fv)$_2$ should be understood to refer to a construct containing two Fv regions and one Fab region joined in any order, i.e. Fab-Fv-Fv, Fv-Fab-Fv, or Fv-Fv-Fab, wherein the last amino acids in one region are followed by the first amino acids in the next region or vice versa. Similarly Fab-(scFv)$_2$ should be understood to refer to a construct containing two scFv regions and one Fab region joined in any order and in the case of the Fab to either polypeptide chain, resulting in 20 possible permutations. Typically these constructs include a peptide linker between the first region (e.g. Fab) and the second region (e.g. Fv). Such linkers are well known in the art, and can be one or more amino acids, typically optimized in length and composition by a skilled artisan. Alternatively said regions may be linked directly, i.e. without a peptide linker. Examples of suitable linker regions for linking a variable domain to a Fab or Fab' are described in WO 2013/068571 incorporated herein by reference, and include, but are not limited to, flexible linker sequences and rigid linker sequences. Antibody fragments can be aglycosylated or glycosylated. The term "antibody fragment" or "antibody fragments" also refers to antibody derivatives that comprise at least one antigen binding or fc receptor binding antibody domain which is covalently linked to another antibody domain, a different protein or a non-protein molecule.

The term "nucleic acid molecule" as used herein refers to a single-stranded or double-stranded nucleic acid. The nucleic acid molecule may be selected from the group comprising a plasmid, an mRNA, a primer and a probe. In an embodiment, the nucleic acid molecule comprises or consist of D-nucleotides. In an alternative embodiment, the nucleic acid molecule comprises or consist of L-nucleotides. The terms "nucleic acid molecule" and "polynucleotide" can be used interchangeably.

The term "polypeptide" as used herein refers to multiple amino acids joined together by peptide bonds. Polypeptides typically comprise from 2 to 100 amino acids, e.g. from 10 to 50 amino acids. Polypeptides may comprise exclusively natural amino acids or may comprise one or more unnatural amino acids, such as β-amino acids (β3 and β2); homo-amino acids; proline and pyruvic acid derivatives; 3-substituted alanine derivatives; glycine derivatives; ring-substituted phenylalanine and tyrosine derivatives; linear core amino acids and N-methyl amino acids.

The term "cation exchange chromatography" as used herein refers to a chromatography wherein the solid phase which is negatively charged, e.g. having one or more negatively charged ligands, such as for example a carboxylate or sulphonate group. Commercially available cation exchange matrices include carboxy-methyl-cellulose, sulphopropyl (SP) immobilized on agarose and sulphonyl immobilized on agarose such as Capto S, Capto Adhere and Capto S Impres (GE Healthcare), Unosphere S and Nuvia S (BioRad), GigaCap S (Tosoh), Fractogel S and Eshmuno S (Merck Millipore) or cation exchange membrane adsorbers such as SartoBind S (Sartorius) and monolith adsorbers such as $SO_3$ monoliths (Bia Separations).

The term "chromatography column" or "column" in connection with chromatography as used herein, refers to a container, frequently in the form of a cylinder or a hollow pillar which is filled with the chromatography matrix. The chromatography matrix is the material which provides the physical and/or chemical properties that are employed for purification.

The term "chromatography cycle" or "operational chromatography cycle" as used herein, refers to the operation of a single cycle of the sequence of process steps on a given allotment of chromatography matrix that may include but is not limited to some to one or more in sequential combination of the following steps: an equilibration step, a reload step, a load step, an overload step, a post load washing step, a secondary washing step, an elution step, a regeneration step, a cleaning step, a storage step and any pause or hold periods. A further cycle may therefore include a repetition of the same sequence of processing steps.

The terms "bind" and "binding" in relation to the interaction of the compound of interest/the target biomolecule to the chromatography matrix refer to the capture of the compound or biomolecule by the matrix. Those skilled in the art will appreciate that the means by which a compound of interest/target biomolecule interacts with a chromatography matrix depends on the nature of the matrix at issue. The term "binds to" does not necessary imply a covalent bonding. For ion exchange chromatography, the "binding" is an ionic interaction between the compound of interest/the target biomolecule and the matrix. For affinity chromatography, the "binding" is an affinity interaction between the compound of interest/the target biomolecule and the matrix. For hydrophobic interaction chromatography, the "binding" is an hydrophobic interaction between the compound of interest/the target biomolecule and the matrix. Relevant binding modes applicable to other types of chromatography will be apparent to those skilled in the art.

The term "dynamic binding capacity" in connection with chromatography as used herein, refers to the amount of protein of interest or other target compound that can bind to a chromatography matrix under a constant flow without having a significant amount of protein of interest or other target compound in the flow through. The dynamic binding capacity of a chromatography matrix is determined by loading a sample containing a known concentration of protein of interest. The load of the protein sample on the column is monitored and will bind to the matrix to a certain break point before unbound protein will flow through the matrix. From the breakthrough curve at a loss of, for example 10% protein, the dynamic binding capacity is found and the experiment is stopped. Often the dynamic binding capacity is defined the amount of protein of interest that can bind to the matrix under a constant flow with not more than 5%, 6%, 7%, 8%, 9%, 10%, 12%, 15%, 17% or 20% of the protein of interest lost in the flow-through, preferably of the concentration of protein of interest being loaded at the same point in time.

The term "flow-through" as used herein, refers to a liquid composition which is obtained by letting a mixture pass through or over a chromatography matrix.

The term "hydrophobic interaction chromatography" as used herein refers to a chromatography wherein the solid phase which is hydrophobic, e.g. having one or more hydrophobic ligands, such as for example a phenyl or butyl group. Commercially available hydrophobic interaction matrices include Phenyl or Butyl immobilized on agarose, such as Capto Phenyl or Capto Butyl (GE Healthcare), ToyoPearl HIC (Tosoh) and Fractogel EMD Phenyl (Merck Millipore), or immobilized on a membrane adsorber such as SartoBind HIC (Sartorius)

The term "membrane adsorber" or "membrane chromatography" in connection with chromatography as used herein, refers to a chromatography format, wherein a semi-permeable membrane is housed in a container through which a feed stream is supplied, and whose surfaces are affixed with resin or ligands which are the materials which provide the physical and/or chemical properties that are employed for purification.

The term "monolith chromatography" or "monolith adsorbers" in connection with chromatography as used herein, refers to a chromatography format, wherein a continuous volume of a porous polymer is housed in a container through which a feed stream is supplied, and whose surfaces are affixed with resin or ligands which is are materials which provide the physical and/or chemical properties that are employed for purification.

The term "mixed-mode" chromatography as used herein refers to a chromatography wherein the solid phase may have a mixture of different charged or uncharged ligands, such as for example hydroxyapatite. Commercially available mixed more matrices include Ceramic Hydroxyapatite (Bio-Rad) or Capto Adhere (GE Healthcare) and HA Ultrogel Hydroxyapatite (Pall).

The term "mixture", as used herein, refers to an at least partially liquid composition comprising at least one protein of interest which is sought to be purified from other substances, such as host cell proteins, DNA or other host cell components, which may also be present. Mixtures can, for example, be suspensions, aqueous solutions, organic solvent systems, or aqueous/organic solvent mixtures or solutions. The mixtures are often complex mixtures or solutions comprising many biological molecules (such as proteins, antibodies, hormones, polynucleotides and viruses), small molecules (such as salts, sugars, lipids, etc.) and even particulate matter. While a typical mixture of biological origin may begin as an aqueous solution or suspension, it may also contain organic solvents used in earlier separation steps such as solvent precipitations, extractions, and the like. As used herein, the term "mixture" may be identified with the term "feedstock". A volume of the mixture/feedstock may be referred to as "feed from the feedstock".

The term "static binding capacity" in connection with chromatography as used herein, refers to the maximal quantity of a protein of interest or other target compound that can bind to a chromatography matrix under static conditions without having a significant amount of protein of interest or other target compound in the flow through. The static binding capacity is normally measured in batch mode in a beaker and is usually referred to as the maximum amount of protein bound to a chromatography medium at given solvent and protein concentration conditions.

The term "pharmaceutically acceptable excipient, diluent or adjuvant" refers to components of therapeutic formulations apart from the product biomolecule. Diluents include e.g. lactose, dextrose, saccharose, cellulose, corn starch or potato starch; Excipients include lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Adjuvants include analgesics, inorganic compounds e.g. alum, aluminum hydroxide, aluminum phosphate, and calcium phosphate hydroxide; mineral oils e.g. paraffin oil; detergents; saponins, cytokines and food based oils. Those skilled in the art are capable of selecting appropriate pharmaceutically acceptable excipients, diluents or adjuvants depending on the application of the product biomolecule.

Further Details

The protein of interest, such as antibody or antibody fragment, that can be purified in accordance with the process of the present invention can be produced by culturing host cells transformed with one or more expression vectors encoding the recombinant antibody or antibody fragment.

Host cells according to the embodiments of the invention are for example prokaryotic, yeast (for example without limitation *Candida boidinii, Hansenula polymorpha, Pichia methanolica, Pichia pastoris, Saccharomyces cerevisiae, Schizosaccharomyces pombe, Kluyveromyces lactis* and other *Kluyveromyces* spp., *Yarrowia lipolytica*), *Myxomycete* (for example without limitation *Dictyostelium discoideum*), filamentous fungi (for example without limitation *Trichoderma reesei* and other *Trichoderma* spp., *Aspergillus niger* and other *Aspergillus* spp.), moss (for example without limitation *Physcomitrella patens, Atrichum undulatum*), insect or mammalian cells. Mammalian host cells are, for example without limitation of NSO, SP2.0, 3T3 cells, COS cells, human osteosarcoma cells, MRC-5 cells, baby hamster kidney (BHK) cells, VERO cells, CHO cells, rCHO-tPA cells, rCHO-Hep B Surface Antigen cells, CHO-S cells, HEK 293 cells, rHEK 293 cells, C127 cells, rC127-Hep B Surface Antigen cells, human fibroblast cells, Stroma cells, hepatocyte cells or PER.C6 cells.

The host cells are preferably eukaryotic host cells, preferably mammalian host cells, more preferably Chinese Hamster Ovary (CHO) cells, e.g. of the DG44 strain.

For eukaryotic host cells (e.g. yeasts, insect or mammalian cells), different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA, can be selected by also introducing one or more markers, which allow for selection of host cells, which contain the expression vector. The marker may also provide for phototrophy to an auxotropic host, biocide resistance, for example without limitation antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

The eukaryotic host cells are transfected with one or more expression vectors encoding the protein of interest and subsequently cultured in any medium that will support their growth and expression of the protein of interest. The medium is a chemically defined medium that is free of animal derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L or 100,000 L, preferably between 5,000 L and 20,000 L, or to 10,000 L. Alternatively, bioreactors of a smaller scale such as between 2 L and 100 L may also be used to manufacture an antibody according to the method of the invention.

A protein of interest, such as an antibody or antigen-binding fragment that is produced in a eukaryotic host cell, such as a CHO cell, in accordance with the process and methods of the present invention is typically found in the supernatant of the cell culture. In an embodiment of the invention said supernatant is the mixture purified in the process of the invention.

Therefore, in a particular embodiment of the invention, the process and methods of the invention comprises a step of centrifugation of the supernatant and recovery of the liquid phase following centrifugation in order to obtain the mixture containing the protein of interest for further purification according to the process of the invention.

Alternatively said supernatant may be recovered using clarification techniques known to the skilled artisan such as for example depth filtration. Therefore, in a particular embodiment for the invention, the method comprises a step of depth filtration in order to obtain the mixture containing the protein of interest for further purification according to the process of the invention.

Alternatively, host cells are prokaryotic cells, preferably gram-negative bacteria, preferably, *E. coli* cells. Prokaryotic cells. Prokaryotic host cells for protein expression are well known in the art. The host cells are recombinant cells which have been genetically engineered to produce the protein of interest such as an antibody fragment. The recombinant *E. coli* host cells may be derived from any suitable *E. coli* strain including from MC4100, TG1, TG2, DHB4, DH5α, DH1, BL21, K12, XL1Blue and JM109. One example is *E. coli* strain W3110 (ATCC 27,325) a commonly used host strain for recombinant protein fermentations. Antibody fragments can also be produced by culturing modified *E. coli* strains, for example metabolic mutants or protease deficient *E. coli* strains.

An antibody fragment that can be purified in accordance with the methods of the present invention is typically found in either the periplasm of the *E. coli* host cell or in the host cell culture supernatant, depending on the nature of the protein, the scale of production and the *E. coli* strain used. The methods for targeting proteins to these compartments are well known in the art. Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter; expression of the recombinant protein can be induced by varying factors such as temperature or the concentration of a particular substance in the growth medium. Examples of inducible promoters include the *E.coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

E. coli host cell cultures (fermentations) may be cultured in any medium that will support the growth of E. coli and expression of the recombinant protein. The medium may be any chemically defined medium such as e.g. described in.

Culturing of the E. coli host cells can take place in any suitable container such as a shake flask or a fermenter depending on the scale of production required. Various large scale fermenters are available with a capacity of more than 1,000 L up to 100,000 L. Preferably, fermenters of between 1,000 L and 50,000 L are used, more preferably of between 1,000 L and 10,000 L or 12,000 L. Smaller scale fermenters may also be used with a capacity of between 0.5 L and 1,000 L.

Fermentation of host cells such as, CHO or E. coli, may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete.

In one embodiment, the process according to the present invention comprises prior to the loading onto the first chromatography matrix a capture step a step of centrifugation of cell culture harvest, followed by suspension of the host cells by addition of the extraction buffer.

For E. coli fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art.

In a particular embodiment of the method of the invention the mixture in the process of the invention according to any embodiment is generated by elution of antibody or antibody fragment bound to Protein A, for example with an elution buffer with a pH suitable to disrupt antibody or antibody fragment binding. Said pH is dependent on the specific molecule and generally determined empirically by the skilled artisan and adjusted to achieve the desired endpoint.

There are many chromatography materials available to the skilled artisan containing said native recombinant Protein A, such as for example MabSelect® (GE Healthcare), Absolute® (Novasep), Captiv A® (Repligen), or Amsphere® (JSR).

Buffers suitable for use as wash and elution buffers in Protein A chromatography are readily available in the art, and may be chosen by way of non-limiting examples from among phosphate buffered saline (PBS), Tris, histidine, acetate, citrate buffers, or MES (2-(N-morpholino)ethanesulphonic acid Imidazole), BES (N,N-(bis-2-hydroxyethyl)-2-aminoethanesulphonic acid), MOPS (3-(N-morpholino)-propanesulphonic acid), or HEPES (N-2-hydroxyethylpiperazine-N'-2-ethanesulphonic acid) buffers.

The following Example illustrates the invention. It does not however, limit the invention in any way. In this regard, it is important to understand that the particular processes described in the Example, and the methods used to demonstrate purity and yield are designed only to provide an indication of the processes of the invention. There are many methods available to determine yield and purity of a biomolecule, and a negative result in any one particular assay is therefore not determinative.

EXAMPLE

Frozen clarified cell culture fluid that had been centrifuged and heat extracted from an E. coli culture containing a naked Fab at a concentration of 2.18 g/L and conductivity of approximately 14 mS/cm was diluted with de-ionised water to a concentration of 0.5 g/L at a pH of approximately 4.5 and conductivity of approximately 3.76 mS/cm. A Bind and Elute chromatography process was performed wherein 3 column volumes (CVs) worth of wash buffer (50 mM Sodium acetate pH 4.5 cond 4.0 mS/cm) was pumped onto a column based chromatographic matrix at 150 cm/h to equilibrate the column, followed by the load containing the proteins of interest applied to a load challenge of 17.5 g/L of the resin volume pumped at 225 cm/hour, followed by another 5 CVs of the same wash buffer at 150 cm/h, followed by a linear elution buffer gradient rising from the low conductivity wash buffer to a high conductivity elution buffer (50 mM Sodium Acetate 225 mM Sodium chloride buffer at pH 4.5 cond 26.4 mS/cm) across 10 CVs at 150 cm/hour, followed by 2 CVs of a high conductivity regeneration buffer (50 mM Sodium Acetate 1M Sodium Chloride pH 4.5 conductivity 85 mS/cm) applied at 300 cm/hour, followed by 2 CVs of a high pH cleaning buffer applied at 300 cm/hour and held at this point for 15 minutes before being rinsed off with an additional 2 CVs of the wash buffer. The chromatography matrix used was a GE 4.66 ml 10 cm Capto S HiScreen cation exchange column the work was performed on a GE Akta Avant machine. Throughout the chromatography conductivity, pH, 280 nm absorbance, 260 nm absorbance and 305 nm absorbance of the output from the column were measured in-line and monitored and recorded in realtime and the output liquid during the 10 CV elution was captured and stored in 1.55 ml fractions in 96-well deep well micro-titre plates at 6 Degrees Celcius. Observing amplitude measurements through the 10 CV gradient elution two main partially separated peaks emerged with a strong overlap; a small peak with a distinct apex around the 17th fraction just before a much larger asymmetric peak apexing at approximately the 22nd fraction. 30 µl of each fraction were sampled and run on an affinity Protein G Analytical HPLC step to determine the composition of the fractions, and integrating the A280 absorbance for the distinct flowthrough peak and the eluate peak on each sample run through the Protein G HPLC allowed distinct determination of the quantity of non-antibody components (the flowthrough on the HPLC, hereon referred to as non-Fab) which corresponded to the early small peak on the Capto S gradient elution and the quantity of antibody components (the eluate on the HPLC, hereon referred to as Fab) which corresponded to the later large peak on the Capto S gradient elution, giving a true profile of both.

The remaining retained volume (representing the vast majority of each fraction—less than 5% from each was used for the Protein G HPLC assay) of two particular fractions (the 21st and 22nd out of 32 total) from the overlapping region between the two peaks in the CEX gradient elution on this first cycle were pooled and added to the same volume of fresh load as on the previous chromatography operation in a container and diluted again to the same conductivity of 3.76 mS/cm using de-ionised water to be loaded again on the next cycle of Capto S chromatography. These fractions were selected because they possessed a high content of the Fab of interest and a significant content of the non-Fab, and effective selection could be assisted by a computer model. (See below). Meanwhile the bulk of the remaining retained volume of the fractions after these selected two (23rd to 31st, hereon referred to as retained pool) and containing predominantly the Fab were pooled and the yielded Fab and remaining impurity in this pool were calculated. In each case Purity for each pool was calculated as the amount of Fab divided by the amount of non-Fab and yield was calculated as the amount of Fab in the retained pool divided by the total Fab in all the fractions covering both elution peaks (fractions 9 to 31).

The combined load/recycled fraction was reapplied to the column in a subsequent 2nd chromatography cycle composed of all the same operations and again the same fractions were collected and the same small portion of each was sampled for assays by Protein G HPLC, and once again, the same two fractions were saved and pooled with additional fresh load to be applied on a 3rd cycle, and again the fractions 23rd through 31st fractions were pooled to calculate the quantity and yield of Fab and non-Fab in this section. This was repeated in the same way for a 3rd and 4th cycle. This resulted in a significant increase in the yield of the Fab in the retained pool in the 2nd, 3rd and 4th cycles that received the recycled fractions from previous cycles by 22%, 23% and 25% respectively compared to the initial cycle which only received raw fresh feed and which was therefore operating as a traditional batch operation and a control for the inventive recycle operation. At the same time the relative purity which was calculated as the ratio of non-Fab per unit of Fab measured in the retained pool remained close to the purity ratio observed in the initial cycle at −4%, −4% and +1%, and after several cycles had equilibrated to the same level as in the initial cycle. Therefore where the retained pool of the first cycle was representative of a traditional chromatographic bind and elute separation giving a particular yield and purity in a given region of retained pool, the subsequent chromatographic cycles incorporating recycled fractions from the previous cycle in accordance with the invention were able to increase the yield of the same region of retained pool while maintaining this purity. By storing the fractions to be recycled in containers, this allowed the yield enhancement of the invention to be achieved on a single chromatographic matrix, and allowed a flexible time gap between separate cycles of the chromatography without substantially affecting the process's ability to equilibrate, which in turn also allowed the time to use offline assays to test the performance amongst the fractions between cycles, and by diluting with fresh load this also precluded the need for a separate dilution buffer for these fractions. Finally the concentration of the retained Fab in the eluate was also boosted in cycles 2, 3 and 4 when compared to the traditional run 1.

The same two fractions selected for recycling were again saved from the 4th cycle to be reapplied on a 5th cycle and in the 5th cycle the fresh load was diluted on its own with de-ionised water to the target conductivity of 3.76 mS/cm in the same way as the 1st cycle before the recycled 21st and 22nd fractions were mixed in, and this time no further deionized water was added to lower the conductivity again to 3.76 mS/cm after the influx of additional salt from the elution buffer contained in the two fractions. As the conductivity of the fresh load to be applied to the next cycle was much lower than required to ensure binding and its volume was much larger than the combined volume of the two recycled fractions, mixing them would have the effect of diluting the high conductivity salt in the fractions sufficiently that it would not prevent binding of the normal bindable components during the loading of the next cycle. In the retained pool of the 5th cycle there was a smaller but still substantial gain in the yield versus the initial (control) cycle at 13% and a slightly reduced but still comparable purity with a loss of 6% with an overall gain in the purity*yield balance of 106%, demonstrating that additional overall performance gains could be achieved even with no additional dilution of the combined feed.

Once again the same two fractions were collected and recycled from the 5th to the 6th cycle, this time with dilution of the combined feed to 3.76 mS/cm as before and in this cycle a significant gain in both yield and purity were achieved in the retained pool at the same time. A final 7th cycle was performed where the 20th, 21st, 22nd and 23rd fractions from the 6th cycle were combined with fresh load and diluted to 3.76 mS/cm with de-ionised water before being loaded in the 7th cycle. In the case that potential future cycles would continue with this new extended range of fractions being recycled the fractions included in the retained pool would necessarily become shorter by one, stretching from the 24th through to the 31st fractions. The retained pool in this case maintained approximately the same yield (97%) and an 8% increased purity when compared to the original retained pool range of the initial cycle demonstrating the ability to increase purity while maintaining yield, and produced 32% greater yield and 11% increased purity compared to a retained pool of the initial cycle that included the same fractions. In the case that cycle would not continue after the 7th, the retained pool including the 23rd through 31st fractions from the 7th cycle gave a 34% greater yield and 12% greater purity compared to the same recycled pool from the initial cycle, demonstrating that both may be boosted significantly.

Purity gain throughout was calculated as the purity of the retained pool in a given cycle divided by the purity of the retained pool in the initial cycle and Yield gain throughout was calculated as the yield of the retained pool in a given cycle divided by the yield of the retained pool in the initial cycle.

Thus it has been demonstrated that recycling select fractions taken from the overlap of partially separated peaks from one cycle into the load of the next can be directed to increase the yield or purity or combinations of both in the remaining non-recycled retained material to enhance the efficient purification of a target product. Rational selection of the fractions to recycle can be aided through computer modeling—after the quantities of the Fab and non-Fab were determined across the samples in the initial cycle a computer model of the peak distributions was created that calculated the amount of Fab and Non-Fab in a given selection of fractions to potentially recycle, and simulated the change in peak composition and quantities in the next retained pool should they be recycled, and through iteration was able to predict the resulting change in purity and yield over multiple cycles. Then the fractions selected for recycle in this simulation were changed to iteratively find conditions that would likely give a boost in purity or yield or both as desired. This process could be driven in either direction to favor either the Fab in the retained pool on one side of the recycled fractions (the late fractions), or Non-Fab on the other side of the recycled fractions (the early fractions). Correspondingly the concentrations of the target product could also be enhanced in the same directed way. This process directed the choice to recycle the 21st and 22nd fractions in the first 6 cycles, and assay data from the 6th cycle was used to recalibrate the simulation which then indicated the recycling of the 20th to 23rd fractions for the 7th cycle.

This recycling approach would naturally extend to any chromatography of any components with peaks that elute with an overlap similar to the described example regardless of whether or not their partial separation was driven by a gradient elution, so long as the separation of the peaks in terms of breakthrough time and peak shape remains the same, as should be the case for any given chromatography where differential separation between mobile components resulting in different breakthrough times and peak shapes is dependent on differential chemical and/or electrostatic interaction between them and the immobilized ligand. Furthermore, this recycling approach would naturally extend to any system with multiple peaks with multiple paired overlaps, such as three sequential peaks having two overlaps or 4 peaks having 3 overlaps or 4 peaks split into two pairs each with one overlap and so on. In each case optimization of the region of each overlap to be recycled onto subsequent cycles can be used to differentially favour the yield (and concentration) and/or purity of a desired component predominant in the retained pool of a target peak relative to an undesired component predominant in the overlapping partner peak, or for instance in the case of a desired component peak surrounded by two overlapping undesired component peaks ahead and behind it, sections of the overlapping regions of both may be recycled to favor the target middle peak over both its neighbors.

The above example shows that by the process according to the invention various advantages may be realized, including enrichment of purity, enhancement of yield, increase of concentration, dilution for free, interruptible operation, single column operation, arbitrary reloading order.

The features of the present invention disclosed in the specification, the claims and/or the drawings may both separately and in any combination thereof be material for realizing the invention in various forms thereof.

REFERENCES

Kontermann, R. E. (2012). "Dual targeting strategies with bispecific antibodies." MAbs 4(2): 182-197.

Mahajan, E., A. George and B. Wolk (2012). "Improving affinity chromatography resin efficiency using semi-continuous chromatography." J Chromatogr A 1227: 154-162.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth follows in the scope of the appended claims.

As used herein, "a" or "an" may mean one or more. The use of the term "or" herein is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, "between X and Y" may mean a range including X and Y.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The following are aspects of the invention:
1. A process for the purification of a compound of interest from a mixture comprising the compound of interest, wherein the process comprises the steps of
a) in a first operational chromatography cycle loading a mixture comprising the compound of interest from a first container to a chromatography matrix operated such that the compound binds to the chromatography matrix;
b) eluting the compound of interest from the chromatography matrix and collecting the eluate containing the compound of interest as fractions of the eluate; and
c) re-loading one or more of the fractions of the eluate to the same chromatography matrix operated such that the compound of interest binds to the chromatography matrix.
2. The process according to aspect 1, wherein the re-loading of step c) is re-loading in a further operational chromatography cycle one or more of the fractions of the eluate to the same chromatography matrix operated such that the compound of interest binds to the chromatography matrix.
3. The process according to aspect 2, wherein the further operational chromatography cycle is the chromatography cycle immediately following.
4. The process according to any one of aspects 1 to 3, wherein the one or more fractions of the eluate re-loaded to the same chromatography matrix are different from one or more fractions of the eluate having a desired characteristic.
5. The process according to aspect 4, wherein the one or more fractions of the eluate re-loaded to the same chromatography matrix is at least one of the one or more fractions of the eluate eluting from the chromatography matrix prior to one or more fractions of the eluate having a desired characteristic, and at least one of the one or more fractions of the eluate eluting from the chromatography matrix after one or more fractions of the eluate having a desired characteristic.

6. The process according to aspect 5, wherein the at least one of the one or more fractions of the eluate eluting from the chromatography matrix prior to one or more fractions of the eluate having a desired characteristic, and the at least one of the one or more fractions of the eluate eluting from the chromatography matrix after one or more fractions of the eluate having a desired characteristic are re-loaded to the same chromatography matrix separately.

7. The process according to aspect 5, wherein the at least one of the one or more fractions of the eluate eluting from the chromatography matrix prior to one or more fractions of the eluate having a desired characteristic, and the at least one of the one or more fractions of the eluate eluting from the chromatography matrix after one or more fractions of the eluate having a desired characteristic are combined and such combined fraction re-loaded to the same chromatography matrix.

8. The process according to any one of aspects 1 to 7, wherein the one or more of the fractions of the eluate are processed prior to or during re-loading, wherein the processed one or more of the fractions of the eluate allow binding of the compound of interest to the chromatography matrix upon re-loading.

9. The process according to any one of aspects 1 to 8, wherein the process comprises, prior to eluting the compound of interest from the chromatography matrix and collecting the eluate containing the compound of interest as fractions of the eluate, the steps of
ab) collecting flow-through containing unbound compound of interest in a second container, and
ac) in a further operational chromatography cycle re-loading the flow-through from the second container to the same chromatography matrix operated such that the compound of interest binds to the chromatography matrix.

10. The process according to any one of aspects 1 to 8, wherein the process comprises, prior to eluting the compound of interest from the chromatography matrix and collecting the eluate containing the compound of interest as fractions of the eluate, the steps of
ab) collecting flow-through containing unbound compound of interest in a second container, and
ac) re-loading the flow-through from the second container to the same chromatography matrix and additionally loading fresh load mixture in a further operational chromatography cycle operated such that the protein of interest binds to the chromatography matrix.

11. The process according to any one of aspects 9 to 10, wherein the flow-through collected in the second container and the one or more of the fractions of the eluate are separately re-loaded in an operational chromatography cycle.

12. The process according to any one of aspects 9 to 10, wherein the flow-through and the one or more of the fractions of the eluate are combined and re-loaded as a combination to the same chromatography matrix operated such that the compound of interest binds to the chromatography matrix.

13. The process according to any one of aspects 1 to 12, wherein the compound of interest is selected from the group comprising a protein, an antibody, an antibody fragment, a nucleic acid molecule and a small molecule.

14. A method of manufacture of a protein of interest comprising the process for purification as defined in any one of aspects 1 to 13, wherein in the process for purification the compound of interest is a protein.

15. A protein, such as an antibody or an antibody fragment, obtained by the method of manufacture of a protein of interest as defined in aspect 14.

The invention claimed is:

1. An industrial-scale process for purification of a product biomolecule from a feedstock comprising the product biomolecule and at least one impurity, the process comprising the steps of: a) loading feed from the feedstock to a chromatography matrix such that the product biomolecule binds to the chromatography matrix; b) eluting the product biomolecule from the chromatography matrix in an eluate by applying an elution solution to the chromatography matrix; wherein the eluate comprises: —a first fraction comprising purified product biomolecule; and—a second fraction comprising both the product biomolecule and at least one impurity, the second fraction comprising one or more leading and/or trailing fraction(s); and wherein the first fraction is collected separately from the second fraction; c) holding the second fraction in one or more container(s); d) loading the second fraction from the container(s) and additional feed from the feedstock to the chromatography matrix such that the product biomolecule in the second fraction binds to the chromatography matrix; wherein the additional feed is loaded simultaneously with or sequentially to the second fraction; and e) eluting the product biomolecule from the chromatography matrix in an eluate by applying an elution solution to the chromatography matrix, wherein the eluate comprises purified product biomolecule; wherein the chromatography matrix in step (a), step (b), step (d) and step (e) is the same chromatography matrix.

2. The process of claim 1, wherein steps (b), (c) and (d) are repeated.

3. The process of claim 1, wherein steps (b), (c) and (d) are performed at least twice.

4. The process of claim 1, wherein the second fraction comprises (i) the leading fraction immediately preceding the first fraction; and/or (ii) the trailing fraction immediately following the first fraction.

5. The process of claim 1, wherein:
steps (a) and (b) are repeated multiple times;
the second fractions collected in each step (b) are pooled together;
step (c) comprises holding the pooled second fractions in the container(s); and
step (d) comprises loading the pooled second fractions from the container(s) to the chromatography matrix such that the product biomolecule in the pooled second fractions binds to the chromatography matrix.

6. The process of claim 1, wherein step (a) further comprises collecting flow-through containing unbound product biomolecule that does not bind to the chromatography matrix; and step (d) further comprises loading the flow-through to the chromatography matrix simultaneously with or sequentially to the second fraction and/or additional feed.

7. The process of claim 1, further comprising processing the second fraction(s) to promote binding of the biomolecule to the chromatography matrix.

8. The process of claim 7, wherein said processing takes place during step (c) and/or step (d).

9. The process of claim 7, wherein said processing comprises altering the pH, ionic strength, concentration, temperature and/or solvent of the second fraction(s) and/or mixing and/or degassing the second fraction(s).

10. The process of claim 1, further comprising testing the second fraction(s).

11. The process of claim 10, wherein testing the second fraction(s) comprises determining one or more of the concentration of the product biomolecule; the concentration of impurities; the identity of impurities; the pH; the ionic strength; the temperature; the solvent; and/or the gas concentration of the second fraction(s).

12. The process of claim 1, wherein step (c) comprises holding the second fraction(s) for at least 5 minutes.

13. The process of claim 12, wherein the chromatography matrix is exchanged, cleaned or renewed during the hold time.

14. The process of claim 1, wherein step (c) comprises holding the second fraction(s) overnight.

15. The process of claim 1, wherein the product biomolecule is a protein, an antibody, an antibody fragment, a polynucleotide or a polypeptide.

16. The process of claim 1, wherein the feedstock has a volume of at least 20 litres, optionally at least 100 litres.

17. The process of claim 1, wherein the chromatography matrix has a bed volume of at least 4 litres.

18. The process of claim 1, wherein in step (b) the volume of the eluate is at least 2 times the bed volume of the chromatography matrix, optionally wherein the volume of the eluate is between 2 times and 20 times the bed volume of the chromatography matrix.

19. The process of claim 1, wherein the chromatography matrix is selected from:
an ion exchange chromatography matrix;
a hydrophobic interaction chromatography matrix;
an affinity chromatography matrix;
a mixed-mode chromatography matrix;
a chiral chromatography matrix; and
a dielectric chromatography matrix.

20. The process of claim 1, wherein the chromatography matrix is in a chromatography column.

21. The process of claim 1, wherein the chromatography matrix is a chromatography membrane or a monolith adsorber.

22. The process of claim 1, wherein eluting the product biomolecule from the chromatography matrix is conducted at a flow rate of at least about 0.2 chromatography matrix volumes per minute.

23. The process of claim 1, further comprising combining each of the first fractions.

24. The process of claim 1, further comprising diafiltering and/or concentrating the purified product biomolecule.

25. The process of claim 1, further comprising nanofiltering the purified product biomolecule.

26. The process of claim 1, further comprising subjecting the purified product biomolecule to further chromatographic purification.

27. The process of claim 1, further comprising chemically modifying the purified product biomolecule.

28. The process of claim 1, further comprising formulating the purified product biomolecule with a pharmaceutically acceptable excipient, diluent or adjuvant.

29. A purified product biomolecule obtainable by the process of claim 1.

* * * * *

UNITED STATES PATENT AND TRADEMARK OFFICE
CERTIFICATE OF CORRECTION

PATENT NO. : 11,498,941 B2
APPLICATION NO. : 16/629609
DATED : November 15, 2022
INVENTOR(S) : Michael Harry Rose It is certified that error appears in the above-identified patent and that said Letters Patent is hereby corrected as shown below:

In the Specification

Column 34,
Line 31, "DH5a," should read --DH5α,--.

Signed and Sealed this
Sixth Day of June, 2023

Katherine Kelly Vidal
*Director of the United States Patent and Trademark Office*